United States Patent
Langevin et al.

(10) Patent No.: US 8,664,245 B2
(45) Date of Patent: Mar. 4, 2014

(54) FUMARATE SALTS OF A HISTAMINE H3 RECEPTOR ANTAGONIST

(75) Inventors: Beverly C. Langevin, Bridgewater, NJ (US); Robert Allan Farr, Bridgewater, NJ (US); Dinubhai H. Shah, Bridgewater, NJ (US); Daniel Sherer, Bridgewater, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/314,772

(22) Filed: Dec. 8, 2011

(65) Prior Publication Data

US 2012/0149728 A1 Jun. 14, 2012

Related U.S. Application Data

(63) Continuation of application No. PCT/US2010/039731, filed on Jun. 24, 2010.

(60) Provisional application No. 61/220,683, filed on Jun. 26, 2009.

(30) Foreign Application Priority Data

Dec. 17, 2009 (FR) ...................................... 09 59110

(51) Int. Cl.
*A01N 43/42* (2006.01)
*A61K 31/47* (2006.01)
*C07D 217/00* (2006.01)

(52) U.S. Cl.
USPC ............................. 514/314; 514/307; 546/139

(58) Field of Classification Search
USPC ............. 514/253.05, 307, 309, 314; 544/128, 544/363; 546/139
See application file for complete search history.

(56) References Cited

U.S. PATENT DOCUMENTS

| 4,228,170 | A | 10/1980 | Bondinell et al. | |
|---|---|---|---|---|
| 4,885,302 | A | 12/1989 | George et al. | |
| 4,925,850 | A | 5/1990 | George et al. | |
| 7,833,999 | B2 * | 11/2010 | Diaz Martin et al. | 514/210.21 |
| 8,273,733 | B2 * | 9/2012 | Diaz Martin et al. | 514/210.21 |
| 2007/0105384 | A1 | 5/2007 | McCutcheon et al. | |
| 2007/0105834 | A1 * | 5/2007 | Diaz Martin et al. | 514/210.21 |
| 2011/0028475 | A1 * | 2/2011 | Diaz Martin et al. | 514/235.2 |

FOREIGN PATENT DOCUMENTS

| EC | SP-06-7020 | 11/2006 |
|---|---|---|
| WO | WO 01/09101 | 2/2001 |
| WO | WO 03/055848 | 7/2003 |
| WO | WO 2005/118547 | 12/2005 |

OTHER PUBLICATIONS

Berge, S. M., et al. Pharmaceutical Salts. Journal of Pharmaceutical Sciences, vol. 66, pp. 1-19. Published 1977.*
Swarbrick, J., et al. Encyclopedia of Pharmaceutical Technology, pp. 453-499. Published 1996.*
Morissette, S.L., et al., Advanced Drug Delivery Reviews vol. 56, pp. 275-300. Published 2004.*
Giovannini, et al., Effects of Histamine H3 Receptor Agonists and Antagonists on Cognitive Performance and Scopolamine-Induced Amnesia, Behavioural Brain Research, vol. 104, pp. 147-155, (1999).
International Search Report for WO2010/151611 dated Dec. 29, 2010.
Giron, Thermal Analysis and Calorimetric Methods in the Characterisation of Polymorphs and Solvates, Thermochimica Acta. vol. 248, (1995), pp. 1-59.
EPO Pub. 1994, Part C, Chapter IV, p. 36, Guidelines for examination in the European Patent Office.
Garcia-Pelayo y Gross R , Larousse Diccionario básico de la lengua española. Ed. Larousse. Buenos Aires, Ragentina. 1979, p. 250 (Spanish definition of the word "form.").
Morrison, et al., Organic Chemistry, FE. As. Mexico, 1976, p. 769.
Raul Moscoso Alvarez, Intellectual Property and Technological Innovation in Ecuador. Ed. Abya-Yala 2000. p. 37.
Remington's Pharmaceutical Sciences, 16th Mack Pub. Co. Pennsylvania. 1980. p, 180-181.
Correa, Guidelines for the examination of pharmaceutical patents: developing a public health perspective, University of Buenos Aires Published by: International Centre for Trade and Sustainable Development (ICTSD), World Health Organization (WHO) Switzerland 2007, p. 9.

* cited by examiner

*Primary Examiner* — Paul Zarek
*Assistant Examiner* — George W Kosturko
(74) *Attorney, Agent, or Firm* — Kelly L. Bender

(57) ABSTRACT

The disclosure relates to fumarate salts of 2-(cyclohexylmethyl)-N-{2-[(2S)-1-methylpyrrolidin-2-yl]ethyl}-1,2,3,4-tetrahydroisoquinoline-7-sulfonamide, to pharmaceutical compositions thereof, processes for making the same, and methods of use thereof.

6 Claims, 9 Drawing Sheets

FUMARATE SALTS OF A HISTAMINE H3 RECEPTOR ANTAGONIST

FIELD OF THE INVENTION

The present invention relates to novel fumarate salt forms of 2-(cyclohexylmethyl)-N-{2-[(2S)-1-methylpyrrolidin-2-yl]ethyl}-1,2,3,4-tetrahydroisoquinoline-7-sulfonamide and pharmaceutical compositions thereof. This invention also relates to processes for the preparation of such salt forms and pharmaceutical compositions, and to methods of use thereof for the prevention and treatment of diseases related to the histamine H3 receptors.

BACKGROUND OF THE INVENTION

The histamine H3 receptors are found in the central and peripheral nervous systems. The administration of histamine H3 receptor ligands may influence the histamine levels or the secretion of neurotransmitters in the brain and the periphery and thus can be useful in the treatment of several disorders, including Alzheimer's disease and other dementias, obesity, central nervous system disorders such as vigilance and sleep disorders, narcolepsy, Parkinson's disease, attention-deficit hyperactivity disorder, memory and learning disorders, epilepsy, schizophrenia, moderate cognitive disorders, depression, anxiety, cardiovascular disorders, and gastrointestinal disorders.

To illustrate, a number of studies in the literature have demonstrated the cognitive enhancing properties of histamine H3 receptors antagonists in rodent models (See, e.g., Giovannini et al., Behav. Brain Res., 104, 147-155 (1999)). These reports further suggest that antagonists and/or inverse agonists could be useful for the treatment of cognitive impairments in neurological diseases such as Alzheimer's disease and related neurodegenerative disorders. Alzheimer's disease is the most common cause of dementia in the elderly, and is often characterized with one or more symptoms such as memory loss, confusion, irritability and aggression, mood swings, language breakdown, long-term memory loss, withdrawal of the sufferer, and loss of motor control.

2-(Cyclohexylmethyl)-N-{2-[(2S)-1-methylpyrrolidin-2-yl]ethyl}-1,2,3,4-tetrahydroisoquinoline-7-sulfonamide, which has the structure of Formula (I):

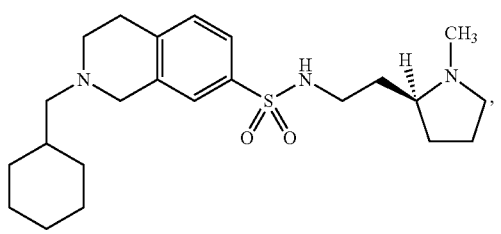

is a potent histamine H3 receptor antagonist with inverse agonist properties. The preparation, physical properties and beneficial pharmacological properties of 2-(cyclohexyl methyl)-N-{2-[(2S)-1-methylpyrrolidin-2-yl]ethyl}-1,2,3,4-tetrahydroisoquinoline-7-sulfonamide are described in, for example, WO2005/118547 (also US2007/0105834). In WO2005/118547, 2-(cyclohexyl methyl)-N-{2-[(2S)-1-methylpyrrolidin-2-yl]ethyl}-1,2,3,4-tetrahydroisoquinoline-7-sulfonamide is described as being in the free base form, which is a viscous oil, or in the form of an oxalate salt, which has low crystallinity and thermal stability.

Although it is known that the preparation of salt forms may improve the physical or pharmaceutical properties of a pharmaceutically active compound, it is not possible to predict which salt forms may possess advantages for a particular purpose prior to the actual preparation and characterization of the salt form. In particular, such advantages, in a non-limiting manner could include, physical forms of the salt in that it provides better processability, solubility or shelf life stability, just to name a few. Other advantages may also include biological properties such as improved bioavailability, reduced adverse reactions at the GI tract (for example irritation of the GI tract, partial degradation of the compound, etc.), or better deliverability of the drug to the intended target site among other advantages.

The present invention therefore provides fumarate salts of 2-(cyclohexylmethyl)-N-{2-[(2S)-1-methylpyrrolidin-2-yl]ethyl}-1,2,3,4-tetrahydroisoquinoline-7-sulfonamide which exhibit advantageous properties which differentiate the fumarate salts from the base form of 2-(cyclohexyl methyl)-N-{2-[(2S)-1-methylpyrrolidin-2-yl]ethyl}-1,2,3,4-tetrahydroisoquinoline-7-sulfonamide itself, and over other salt forms of 2-(cyclohexylmethyl)-N-{2-[(2S)-1-methylpyrrolidin-2-yl]ethyl}-1,2,3,4-tetrahydroisoquinoline-7-sulfonamide known in the art.

Furthermore, the crystallinity and stability profile of the difumarate monohydrate salt of 2-(cyclohexyl methyl)-N-{2-[(2S)-1-methylpyrrolidin-2-yl]ethyl}-1,2,3,4-tetrahydroisoquinoline-7-sulfonamide make this solid form unpredictably and particularly useful as a medicament.

SUMMARY OF THE INVENTION

Accordingly, the present invention is directed to the fumarate salts of 2-(cyclohexylmethyl)-N-{2-[(2S)-1-methylpyrrolidin-2-yl]ethyl}-1,2,3,4-tetrahydroisoquinoline-7-sulfonamide. The present invention is also directed to novel crystalline forms of the fumarate salts of 2-(cyclohexyl methyl)-N-{2-[(2S)-1-methylpyrrolidin-2-yl]ethyl}-1,2,3,4-tetrahydroisoquinoline-7-sulfonamide.

One aspect of the invention is the difumarate monohydrate salt of 2-(cyclohexylmethyl)-N-{2-[(2S)-1-methylpyrrolidin-2-yl]ethyl}-1,2,3,4-tetrahydroisoquinoline-7-sulfonamide (designated "the difumarate monohydrate salt"), represented by Formula (II):

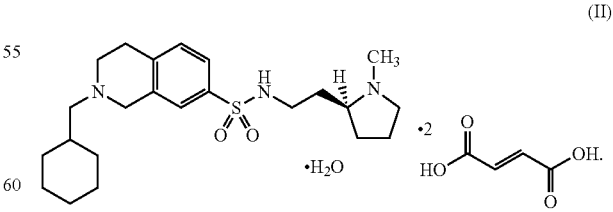

Another aspect of the invention is the difumarate salt of 2-(cyclohexylmethyl)-N-{2-[(2S)-1-methylpyrrolidin-2-yl]ethyl}-1,2,3,4-tetrahydroisoquinoline-7-sulfonamide (designated "the difumarate salt"), represented by Formula (III):

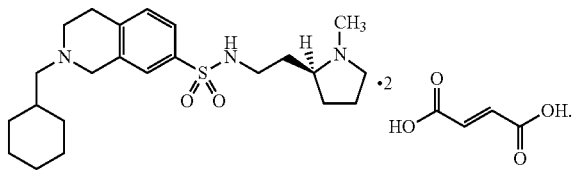

(III)

Another aspect of the invention is the monofumarate salt of 2-(cyclohexylmethyl)-N-{2-[(2S)-1-methylpyrrolidin-2-yl]ethyl}-1,2,3,4-tetrahydroisoquinoline-7-sulfonamide (designated "the monofumarate salt"), represented by Formula (IV):

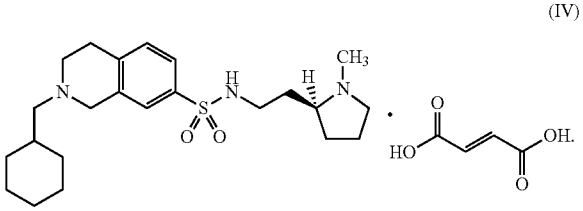 [SMILES: CN1CCC[C@H]1CCNS(=O)(=O)c1ccc2c(c1)CN(CC1CCCCC1)CC2 ; O=C(O)/C=C/C(=O)O]

(IV)

Another aspect of the invention is the hemifumarate dihydrate salt of 2-(cyclohexylmethyl)-N-{2-[(2S)-1-methylpyrrolidin-2-yl]ethyl}-1,2,3,4-tetrahydroisoquinoline-7-sulfonamide (designated "the hemifumarate dihydrate salt"), represented by Formula (V):

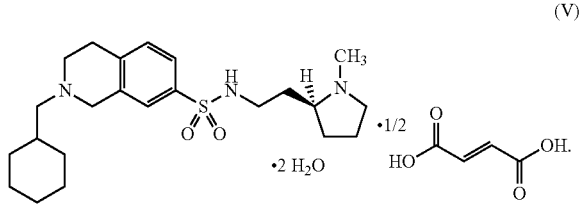 [SMILES: CN1CCC[C@H]1CCNS(=O)(=O)c1ccc2c(c1)CN(CC1CCCCC1)CC2 ; "·2 H2O" ; O=C(O)/C=C/C(=O)O]

(V)

Another aspect of the invention is the hemifumarate salt of 2-(cyclohexylmethyl)-N-{2-[(2S)-1-methylpyrrolidin-2-yl]ethyl}-1,2,3,4-tetrahydroisoquinoline-7-sulfonamide (designated "the hemifumarate salt"), represented by Formula (VI):

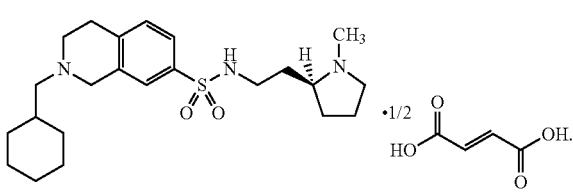

(VI)

Another aspect of the present invention is a pharmaceutical composition comprising one or more compounds of the invention and a pharmaceutically acceptable carrier.

Another aspect of the invention is a pharmaceutical composition prepared by formulating one or more compounds of the invention with one or more pharmaceutically acceptable carriers.

Another aspect of the invention is a process for preparing a pharmaceutical composition of 2-(cyclohexylmethyl)-N-{2-[(2S)-1-methylpyrrolidin-2-yl]ethyl}-1,2,3,4-tetrahydroisoquinoline-7-sulfonamide comprising formulating one or more compounds of the invention with one or more pharmaceutically acceptable diluents.

Another aspect of the present invention is a method of treating a pathology in which a histamine H3 receptor antagonist provides a therapeutic benefit.

The present invention is more fully discussed with the aid of the following figures and detailed description below.

DETAILED DESCRIPTION OF THE INVENTION

Definitions and Abbreviations

As used above, and throughout the description of the invention, the following abbreviations, unless otherwise indicated, shall be understood to have the following meanings:

DMF N,N-dimethylformamide
ETOH ethanol
g gram
HPLC high performance liquid chromatography
mg milligram
mL milliliter
uL microliter
MTBE tert-butyl methyl ether
NMR nuclear magnetic resonance
RH relative humidity As used above, and throughout the description of the invention, various terms used herein shall have the generally accepted meanings in the art. More particularly, the following terms, unless otherwise indicated, shall generally be understood to have the following meanings.

The "difumarate monohydrate salt," as used herein, is meant to describe the difumarate monohydrate salt of 2-(cyclohexylmethyl)-N-{2-[(2S)-1-methylpyrrolidin-2-yl]ethyl}-1,2,3,4-tetrahydroisoquinoline-7-sulfonamide that may be characterized using distinguishing data as described herein. Exemplary data is found in FIGS. 1, 2, 3 and 8. The difumarate monohydrate salt of 2-(cyclohexylmethyl)-N-{2-[(2S)-1-methylpyrrolidin-2-yl]ethyl}-1,2,3,4-tetrahydroisoquinoline-7-sulfonamide is also synonymously called 2-(cyclohexylmethyl)-N-{2-[(2S)-1-methylpyrrolidin-2-yl]ethyl}-1,2,3,4-tetrahydroisoquinoline-7-sulfonamide difumarate hydrate and 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

Figure 1:
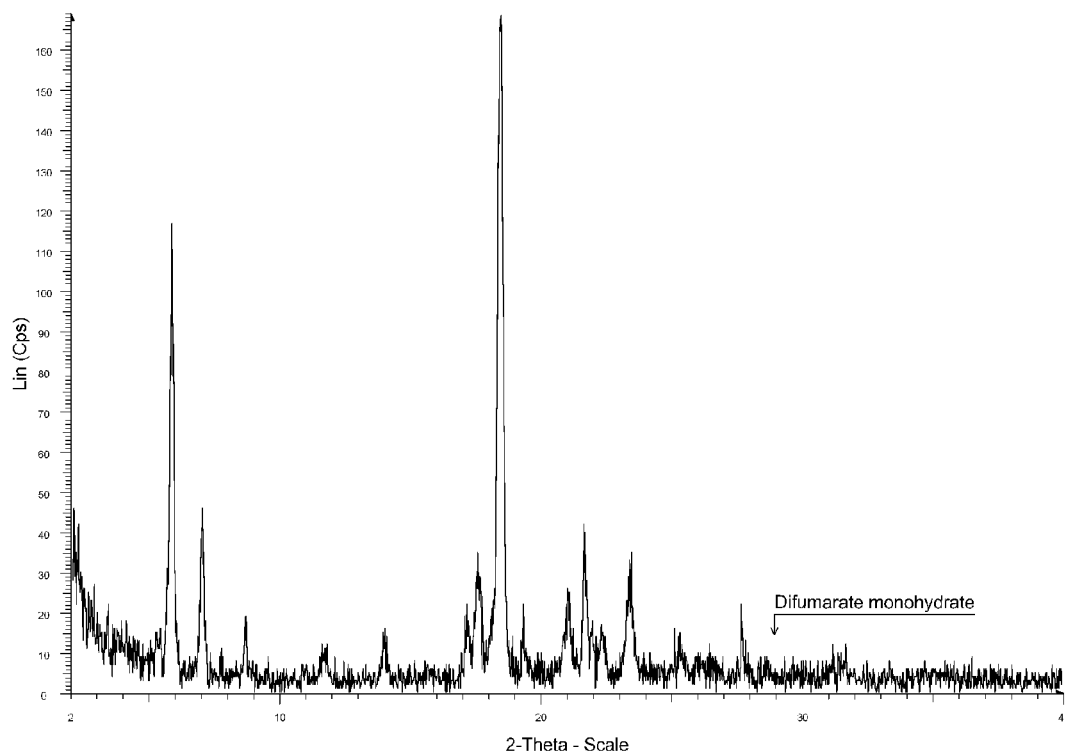
FIG. 1 is an X-ray powder diffractogram of crystalline 2-(cyclohexylmethyl)-N-{2-[(2S)-1-methylpyrrolidin-2-yl]ethyl}-1,2,3,4-tetrahydroisoquinoline-7-sulfonamide difumarate monohydrate of the present invention.
Figure 2:
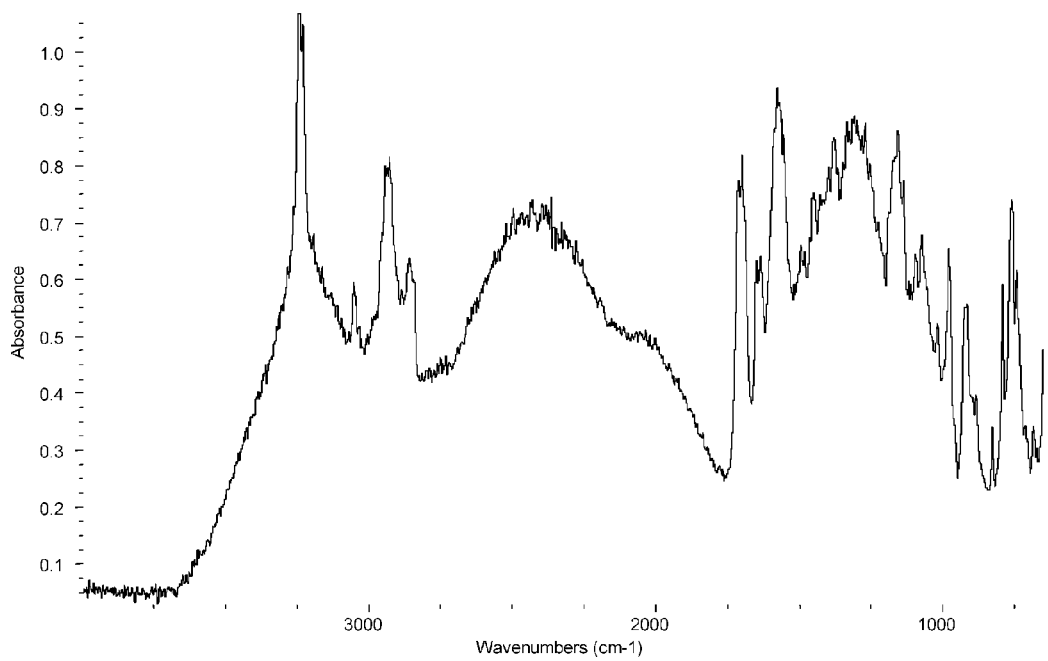
FIG. 2 is a Fourier Transform Infrared (FTIR) spectrum of 2-(cyclohexylmethyl)-N-{2-[(2S)-1-methylpyrrolidin-2-yl]ethyl}-1,2,3,4-tetrahydroisoquinoline-7-sulfonamide difumarate monohydrate of the present invention.
Figure 3:
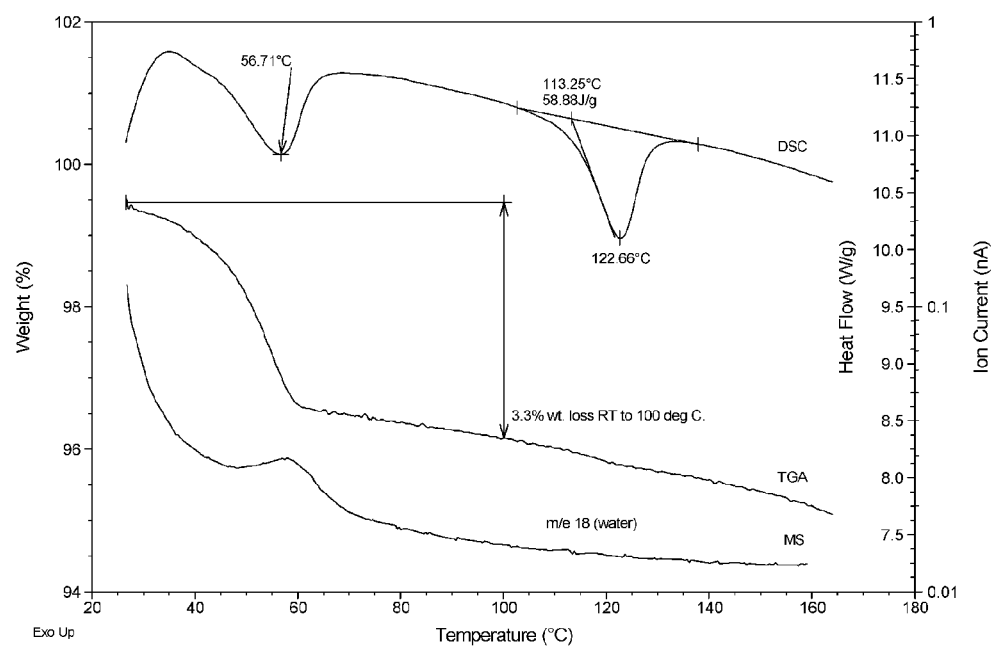
FIG. 3 is a Differential Scanning calorimetry—Thermal Gravimetric Analysis and Mass Spectrometry (DSC-TGA-MS) thermogram of 2-(cyclohexylmethyl)-N-{2-[(2S)-1-methylpyrrolidin-2-yl]ethyl}-1,2,3,4-tetrahydroisoquinoline-7-sulfonamide difumarate monohydrate of the present invention.
Figure 4:
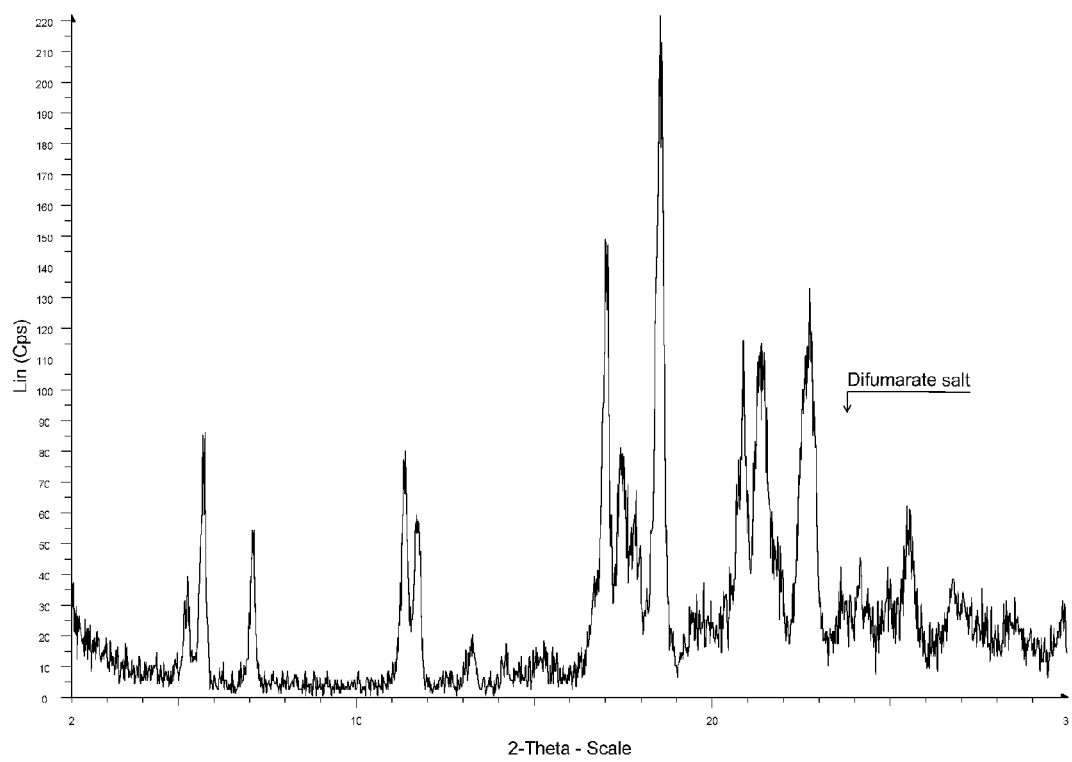
FIG. 4 is an X-ray powder diffractogram of crystalline 2-(cyclohexylmethyl)-N-{2-[(2S)-1-methylpyrrolidin-2-yl]ethyl}-1,2,3,4-tetrahydroisoquinoline-7-sulfonamide difumarate of the present invention.

The "difumarate salt," as used herein, is meant to describe the difumarate salt of 2-(cyclohexyl methyl)-N-{2-[(2S)-1-methylpyrrolidin-2-yl]ethyl}-1,2,3,4-tetrahydroisoquinoline-7-sulfonamide that may be characterized using distinguishing data as described herein. Exemplary data is found in FIGS. 4 and 8. The difumarate salt of 2-(cyclohexylmethyl)-N-{2-[(2S)-1-methylpyrrolidin-2-yl]ethyl}-1,2,3,4-tetrahydroisoquinoline-7-sulfonamide is also synonymously called 2-(cyclohexylmethyl)-N-{2-[(2S)-1-methylpyrrolidin-2-yl]ethyl}-1,2,3,4-tetrahydroisoquinoline-7-sulfonamide difumarate, anhydrous 2-(cyclohexylmethyl)-N-{2-[(2S)-1-methylpyrrolidin-2-yl]ethyl}-1,2,3,4-tetrahydroisoquinoline-7-sulfonamide difumarate, 2-(cyclohexyl methyl)-N-{2-[(2S)-1-methylpyrrolidin-2-yl]ethyl}-1,2,3,4-tetrahydroisoquinoline-7-sulfonamide difumarate anhydrate, and the difumarate anhydrate.

The "monofumarate salt," as used herein, is meant to describe the monofumarate salt of 2-(cyclohexyl methyl)-N-{2-[(2S)-1-methylpyrrolidin-2-yl]ethyl}-1,2,3,4-tetrahydroisoquinoline-7-sulfonamide that may be characterized using distinguishing data as described herein. Exemplary data is found in FIGS. 5 and 6. The monofumarate salt of 2-(cyclohexylmethyl)-N-{2-[(2S)-1-methylpyrrolidin-2-yl]ethyl}-1,2,3,4-tetrahydroisoquinoline-7-sulfonamide is also synonymously called 2-(cyclohexylmethyl)-N-{2-[(2S)-1-methylpyrrolidin-2-yl]ethyl}-1,2,3,4-tetrahydroisoquinoline-7-sulfonamide monofumarate.

The "hemifumarate salt," as used herein, is meant to describe the hemifumarate salt of 2-(cyclohexyl methyl)-N-{2-[(2S)-1-methylpyrrolidin-2-yl]ethyl}-1,2,3,4-tetrahydroisoquinoline-7-sulfonamide that may be characterized using distinguishing data as described herein. Exemplary data is found in FIGS. 6, 7, and 9. The hemifumarate salt of 2-(cyclohexyl methyl)-N-{2-[(2S)-1-methylpyrrolidin-2-yl]ethyl}-1,2,3,4-tetrahydroisoquinoline-7-sulfonamide is also synonymously called 2-(cyclohexylmethyl)-N-{2-[(2S)-1-methylpyrrolidin-2-yl]ethyl}-1,2,3,4-tetrahydroisoquinoline-7-sulfonamide hemifumarate, 2-(cyclohexylmethyl)-N-{2-[(2S)-1-methylpyrrolidin-2-yl]ethyl}-1,2,3,4-tetrahydroisoquinoline-7-sulfonamide hemifumarate dehydrate, anhydrous 2-(cyclohexylmethyl)-N-{2-[(2S)-1-methylpyrrolidin-2-yl]ethyl}-1,2,3,4-tetrahydroisoquinoline-7-sulfonamide hemifumarate, and the hemifumarate anhydrate salt.

The "hemifumarate dihydrate salt," as used herein, is meant to describe the hemifumarate dihydrate salt of 2-(cyclohexylmethyl)-N-{2-[(2S)-1-methylpyrrolidin-2-yl]ethyl}-1,2,3,4-tetrahydroisoquinoline-7-sulfonamide that may be characterized using distinguishing data as described herein. Exemplary data is found in FIGS. 6, 7 and 9. The hemifumarate dihydrate salt of 2-(cyclohexylmethyl)-N-{2-[(2S)-1-methylpyrrolidin-2-yl]ethyl}-1,2,3,4-tetrahydroisoquinoline-7-sulfonamide is also synonymously called 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate.

"Compounds of the invention," as used herein, is meant to describe 2-(cyclohexylmethyl)-N-{2-[(2S)-1-methylpyrrolidin-2-yl]ethyl}-1,2,3,4-tetrahydroisoquinoline-7-sulfonamide difumarate monohydrate, 2-(cyclohexylmethyl)-N-{2-[(2S)-1-methylpyrrolidin-2-yl]ethyl}-1,2,3,4-tetrahydroisoquinoline-7-sulfonamide difumarate, 2-(cyclohexylmethyl)-N-{2-[(2S)-1-methylpyrrolidin-2-yl]ethyl}-1,2,3,4-tetrahydroisoquinoline-7-sulfonamide monofumarate, 2-(cyclohexyl methyl)-N-{2-[(2S)-1-methylpyrrolidin-2-yl]ethyl}-1,2,3,4-tetrahydroisoquinoline-7-sulfonamide hemifumarate, and 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate.

"Treating" or "treatment" means to alleviate or partially alleviate symptoms, eliminate the causation of the symptoms either on a temporary or permanent basis, or to slow the appearance of symptoms of the named disorder or condition. The compounds and compositions of this invention are useful in treating a pathology in which a histamine H3 receptor antagonist provides a therapeutic benefit. For example, the treatment of Alzheimer's disease may include reversing disease progression, improving memory and/or cognition; and slowing the loss of memory and/or cognition.

"Patient" includes both human and other mammals.

"Pharmaceutically effective amount" is meant to describe an amount of a compound, composition, medicament or other active ingredient effective in producing the desired therapeutic effect.

The present invention provides a process for the manufacture of the 2-(cyclohexylmethyl)-N-{2-[(2S)-1-methylpyrrolidin-2-yl]ethyl}-1,2,3,4-tetrahydroisoquinoline-7-sulfonamide difumarate monohydrate of formula (II), said process comprising the steps of contacting, under elevated temperature or at ambient temperature, 2-(cyclohexylmethyl)-N-{2-[(2S)-1-methylpyrrolidin-2-yl]ethyl}-1,2,3,4-tetrahydroisoquinoline-7-sulfonamide dissolved in a suitable solvent or in a mixture of solvents, with fumaric acid, optionally dissolved in a solvent or in a mixture of solvents, and isolating the precipitated solid, for example by filtration or removal of the solvent. In one embodiment, about two moles of fumaric acid are reacted per mole of 2-(cyclohexylmethyl)-N-{2-[(2S)-1-methylpyrrolidin-2-yl]ethyl}-1,2,3,4-tetrahydroisoquinoline-7-sulfonamide. In another embodiment, greater than two moles of fumaric acid are reacted per mole of 2-(cyclohexylmethyl)-N-{2-[(2S)-1-methylpyrrolidin-2-yl]ethyl}-1,2,3,4-tetrahydroisoquinoline-7-sulfonamide.

Suitable solvents to dissolve 2-(cyclohexylmethyl)-N-{2-[(2S)-1-methylpyrrolidin-2-yl]ethyl}-1,2,3,4-tetrahydroisoquinoline-7-sulfonamide for performing the salt formation comprise alcohols, for example methanol, ethanol, 1- or 2-propanol, isomeric alcohols of butanol, isomeric alcohols of pentanol, and isomeric alcohols of hexanol, like 2-methyl-4-pentanol; ketones like acetone; ethers, for example tetrahydrofuran and dioxane; acetic acid esters, for example ethyl acetate; organic acids, for example acetic acid; amides, for example N-methylpyrrolidinone and nitriles, for example acetonitrile; and mixtures thereof including mixtures comprising water.

Also provided is a process for preparing 2-(cyclohexylmethyl)-N-{2-[(2S)-1-methylpyrrolidin-2-yl]ethyl}-1,2,3,4-tetrahydroisoquinoline-7-sulfonamide difumarate monohydrate comprising contacting 2-(cyclohexylmethyl)-N-{2-[2S)-1-methylpyrrolidin-2-yl]ethyl}-1,2,3,4-tetrahydroisoquinoline-7-sulfonamide difumarate with water.

Another aspect of the invention, is the process for preparing 2-(cyclohexylmethyl)-N-{2-[(2S)-1-methylpyrrolidin-2-yl]ethyl}-1,2,3,4-tetrahydroisoquinoline-7-sulfonamide difumarate monohydrate comprising exposing 2-(cyclohexylmethyl)-N-{2-[(2S)-1-methylpyrrolidin-2-yl]ethyl}-1,2,3,4-tetrahydroisoquinoline-7-sulfonamide difumarate to above about 10% relative humidity at around ambient temperature, wherein ambient temperature ranges from 20 to 25° C.

A particular aspect of the invention is 2-(cyclohexylmethyl)-N-{2-[(2S)-1-methylpyrrolidin-2-yl]ethyl}-1,2,3,4-tetrahydroisoquinoline-7-sulfonamide difumarate monohydrate in crystalline form. The crystalline form of 2-(cyclohexylmethyl)-N-{2-[(2S)-1-methylpyrrolidin-2-yl]ethyl}-1,2,3,4-tetrahydroisoquinoline-7-sulfonamide difumarate monohydrate described in this specification is referred to as 2-(cyclohexylmethyl)-N-{2-[(2S)-1-methylpyrrolidin-2-yl]ethyl}-1,2,3,4-tetrahydroisoquinoline-7-sulfonamide difumarate monohydrate Form I. In one aspect of the invention, the crystalline form of 2-(cyclohexylmethyl)-N-{2-[(2S)-1-methylpyrrolidin-2-yl]ethyl}-1,2,3,4-tetrahydroisoquinoline-7-sulfonamide difumarate monohydrate exhibits an X-ray diffraction pattern comprising peaks at about 5.31, 5.84, 7.00, and 8.67 degrees 2-theta.

Another particular aspect of the invention is a process for preparing 2-(cyclohexylmethyl)-N-{2-[(2S)-1-methylpyrrolidin-2-yl]ethyl}-1,2,3,4-tetrahydroisoquinoline-7-sulfonamide difumarate monohydrate in crystalline form.

To obtain 2-(cyclohexyl methyl)-N-{2-[(2S)-1-methylpyrrolidin-2-yl]ethyl}-1,2,3,4-tetrahydroisoquinoline-7-sulfonamide difumarate monohydrate in crystalline form, 2-(cyclohexyl methyl)-N-{2-[(2S)-1-methylpyrrolidin-2-yl]ethyl}-1,2,3,4-tetrahydroisoquinoline-7-sulfonamide is dissolved in a suitable solvent or in a mixture of solvents, including but not limited to methanol, ethanol, isopropanol, acetonitrile, acetone, and water with fumaric acid, optionally dissolved in a solvent or in a mixture of solvents, and isolating the precipitated solid, for example by filtration or removal of the solvent by vacuum drying. In one embodiment, 1 mole of fumaric acid is reacted per mole of 2-(cyclohexylmethyl)-N-{2-[(2S)-1-methylpyrrolidin-2-yl]ethyl}-1,2,3,4-tetrahydroisoquinoline-7-sulfonamide. In another embodiment, two moles of fumaric acid are reacted per mole of 2-(cyclohexylmethyl)-N-{2-[(2S)-1-methylpyrrolidin-2-yl]ethyl}-1,2,3,4-tetrahydroisoquinoline-7-sulfonamide.

For a better control of the crystallization, it is possible to provide a step of initiating the crystallization, carried out by seeding the reaction medium with a small amount of 2-(cyclohexyl methyl)-N-{2-[(2S)-1-methylpyrrolidin-2-yl]ethyl}-1,2,3,4-tetrahydroisoquinoline-7-sulfonamide difumarate monohydrate previously obtained in crystalline form, such as described above. For this seeding, it is possible to use, for example, a weight percentage of 2-(cyclohexylmethyl)-N-{2-[(2S)-1-methylpyrrolidin-2-yl]ethyl}-1,2,3,4-tetrahydroisoquinoline-7-sulfonamide difumarate monohydrate between 0.05% and 5% relative to the total amount of 2-(cyclohexylmethyl)-N-{2-[(2S)-1-methylpyrrolidin-2-yl]ethyl}-1,2,3,4-tetrahydroisoquinoline-7-sulfonamide in base form to be reacted. For example, about 0.1 wt % of 2-(cyclohexylmethyl)-N-{2-[(2S)-1-methylpyrrolidin-2-yl]ethyl}-1,2,3,4-tetrahydroisoquinoline-7-sulfonamide difumarate monohydrate could be used relative to the total amount of 2-(cyclohexylmethyl)-N-{2-[(2S)-1-methylpyrrolidin-2-yl]ethyl}-1,2,3,4-tetrahydroisoquinoline-7-sulfonamide in base form to be reacted.

Another aspect of the invention is 2-(cyclohexylmethyl)-N-{2-[(2S)-1-methylpyrrolidin-2-yl]ethyl}-1,2,3,4-tetrahydroisoquinoline-7-sulfonamide difumarate. This difumarate salt is particularly useful for the preparation of the difumarate monohydrate salt.

A particular aspect of the invention is 2-(cyclohexylmethyl)-N-{2-[(2S)-1-methylpyrrolidin-2-yl]ethyl}-1,2,3,4-tetrahydroisoquinoline-7-sulfonamide difumarate in crystalline form. The crystalline form of 2-(cyclohexylmethyl)-N-{2-[(2S)-1-methylpyrrolidin-2-yl]ethyl}-1,2,3,4-tetrahydroisoquinoline-7-sulfonamide difumarate described in this specification is referred to as 2-(cyclohexylmethyl)-N-{2-[(2S)-1-methylpyrrolidin-2-yl]ethyl}-1,2,3,4-tetrahydroisoquinoline-7-sulfonamide difumarate Form I. In one aspect of the invention, the crystalline form of 2-(cyclohexylmethyl)-N-{2-[(2S)-1-methylpyrrolidin-2-yl]ethyl}-1,2,3,4-tetrahydroisoquinoline-7-sulfonamide difumarate exhibits an X-ray diffraction pattern comprising peaks at about 5.21, 5.67, 7.06, and 11.34 degrees 2-theta.

The present invention also provides a process for preparing 2-(cyclohexylmethyl)-N-{2-[(2S)-1-methylpyrrolidin-2-yl]ethyl}-1,2,3,4-tetrahydroisoquinoline-7-sulfonamide difumarate, comprising dehydrating 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

In one aspect of the invention, a process for preparing 2-(cyclohexylmethyl)-N-{2-[(2S)-1-methylpyrrolidin-2-yl]ethyl}-1,2,3,4-tetrahydroisoquinoline-7-sulfonamide difumarate comprises exposing 2-(cyclohexylmethyl)-N-{2-[(2S)-1-methylpyrrolidin-2-yl]ethyl}-1,2,3,4-tetrahydroisoquinoline-7-sulfonamide difumarate monohydrate to low relative humidity, for example below about 10% humidity for two or more hours at around ambient temperature, wherein ambient temperature ranges from 20 to 25° C.

In another aspect of the invention, a process for preparing 2-(cyclohexylmethyl)-N-{2-[(2S)-1-methylpyrrolidin-2-yl]ethyl}-1,2,3,4-tetrahydroisoquinoline-7-sulfonamide difumarate comprises heating 2-(cyclohexylmethyl)-N-{2-[(2S)-1-methylpyrrolidin-2-yl]ethyl}-1,2,3,4-tetrahydroisoquinoline-7-sulfonamide difumarate monohydrate above about 75° C.

In another aspect of the invention, a process for preparing 2-(cyclohexylmethyl)-N-{2-[(2S)-1-methylpyrrolidin-2-yl]ethyl}-1,2,3,4-tetrahydroisoquinoline-7-sulfonamide difumarate comprises heating 2-(cyclohexylmethyl)-N-{2-[(2S)-1-methylpyrrolidin-2-yl]ethyl}-1,2,3,4-tetrahydroisoquinoline-7-sulfonamide difumarate monohydrate above room temperature, for example above about 40° C., at low relative humidity, for example below about 10% humidity.

Another aspect of the invention is 2-(cyclohexylmethyl)-N-{2-[(2S)-1-methylpyrrolidin-2-yl]ethyl}-1,2,3,4-tetrahydroisoquinoline-7-sulfonamide monofumarate. A particular aspect of the invention is 2-(cyclohexylmethyl)-N-{2-[(2S)-1-methylpyrrolidin-2-yl]ethyl}-1,2,3,4-tetrahydroisoquinoline-7-sulfonamide monofumarate in crystalline form. The crystalline form of 2-(cyclohexylmethyl)-N-{2-[(2S)-1-methylpyrrolidin-2-yl]ethyl}-1,2,3,4-tetrahydroisoquinoline-7-sulfonamide monofumarate described in this specification is referred to as 2-(cyclohexylmethyl)-N-{2-[(2S)-1-methylpyrrolidin-2-yl]ethyl}-1,2,3,4-tetrahydroisoquinoline-7-sulfonamide monofumarate Form I. In one aspect of the invention, the crystalline form of 2-(cyclohexylmethyl)-N-{2-[(2S)-1-methylpyrrolidin-2-yl]ethyl}-1,2,3,4-tetrahydroisoquinoline-7-sulfonamide monofumarate exhibits an X-ray diffraction pattern comprising peaks at about 3.37, 6.70, 13.36, 14.83, 15.88, and 17.65 degrees 2-theta.

The present invention also provides a process for preparing 2-(cyclohexylmethyl)-N-{2-[(2S)-1-methylpyrrolidin-2-yl]ethyl}-1,2,3,4-tetrahydroisoquinoline-7-sulfonamide monofumarate, comprising contacting, under elevated temperature or at ambient temperature 2-(cyclohexylmethyl)-N-{2-[(2S)-1-methylpyrrolidin-2-yl]ethyl}-1,2,3,4-tetrahydroisoquinoline-7-sulfonamide dissolved in a suitable solvent or in a mixture of solvents, with one equivalent of fumaric acid, optionally dissolved in a solvent or in a mixture of solvents, and isolating the precipitated difumarate monohydrate solid, for example by filtration or removal of the solvent. The monofumarate salt may be obtained after successive crystallizations from the mother liquor.

Suitable solvents to dissolve 2-(cyclohexylmethyl)-N-{2-[(2S)-1-methylpyrrolidin-2-yl]ethyl}-1,2,3,4-tetrahydroisoquinoline-7-sulfonamide for performing the monofumarate salt formation comprise alcohols, for example methanol, ethanol, 1- or 2-propanol, isomeric alcohols of butanol, isomeric alcohols of pentanol, and isomeric alcohols of hexanol, like 2-methyl-4-pentanol; ketones like acetone; ethers, for example tetrahydrofuran and dioxane; acetic acid esters, for example ethyl acetate; organic acids, for example acetic acid; amides, for example N-methylpyrrolidinone and nitriles, for example acetonitrile; and mixtures thereof including mixtures comprising water.

Another aspect of the invention is 2-(cyclohexylmethyl)-N-{2-[(2S)-1-methylpyrrolidin-2-yl]ethyl}-1,2,3,4-tetrahydroisoquinoline-7-sulfonamide hemifumarate. A particular aspect of the invention is 2-(cyclohexylmethyl)-N-{2-[(2S)-1-methylpyrrolidin-2-yl]ethyl}-1,2,3,4-tetrahydroisoquinoline-7-sulfonamide hemifumarate in crystalline form. The crystalline form of 2-(cyclohexylmethyl)-N-{2-[(2S)-1-methylpyrrolidin-2-yl]ethyl}-1,2,3,4-tetrahydroisoquinoline-7-sulfonamide hemifumarate described in this specification is referred to as 2-(cyclohexylmethyl)-N-{2-[(2S)-1-methylpyrrolidin-2-yl]ethyl}-1,2,3,4-tetrahydroisoquinoline-7-sulfonamide hemifumarate Form I. In one aspect of the invention, the crystalline form of 2-(cyclohexylmethyl)-N-{2-[(2S)-1-methylpyrrolidin-2-yl]ethyl}-1,2,3,4-tetrahydroisoquinoline-7-sulfonamide hemifumarate exhibits an X-ray diffraction pattern comprising peaks at about 3.61, 7.22, 7.96, 8.21, 9.01, 10.82, and 15.66 degrees 2-theta.

The present invention also provides a process for preparing 2-(cyclohexylmethyl)-N-{2-[(2S)-1-methylpyrrolidin-2-yl]ethyl}-1,2,3,4-tetrahydroisoquinoline-7-sulfonamide hemifumarate, comprising the steps of contacting, under elevated temperature or at ambient temperature, 2-(cyclohexylmethyl)-N-{2-[(2S)-1-methylpyrrolidin-2-yl]ethyl}-1,2,3,4-tetrahydroisoquinoline-7-sulfonamide dissolved in a suitable solvent or in a mixture of solvents, with fumaric acid, optionally dissolved in a solvent or in a mixture of solvents, and isolating the precipitated solid, for example by filtration or removal of the solvent, and drying. The hemifumarate salt may be obtained after successive crystallizations from the mother liquor.

Suitable solvents to dissolve 2-(cyclohexylmethyl)-N-{2-[(2S)-1-methylpyrrolidin-2-yl]ethyl}-1,2,3,4-tetrahydroisoquinoline-7-sulfonamide for performing the hemifumarate salt formation comprise alcohols, for example methanol, ethanol, 1- or 2-propanol, isomeric alcohols of butanol, isomeric alcohols of pentanol, and isomeric alcohols of hexanol, like 2-methyl-4-pentanol; ketones like acetone; ethers, for example tetrahydrofuran and dioxane; acetic acid esters, for example ethyl acetate; organic acids, for example acetic acid; amides, for example N-methylpyrrolidinone and nitriles, for example acetonitrile; and mixtures thereof including mixtures comprising water.

The present invention also provides a process for preparing 2-(cyclohexylmethyl)-N-{2-[(2S)-1-methylpyrrolidin-2-yl]ethyl}-1,2,3,4-tetrahydroisoquinoline-7-sulfonamide hemifumarate, comprising dehydrating 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate.

In one aspect of the invention, a process for preparing 2-(cyclohexylmethyl)-N-{2-[(2S)-1-methylpyrrolidin-2-yl]ethyl}-1,2,3,4-tetrahydroisoquinoline-7-sulfonamide hemifumarate comprises exposing 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate to low relative humidity, for example below about 10% humidity for two or more hours.

In another aspect of the invention, a process for preparing 2-(cyclohexylmethyl)-N-{2-[(2S)-1-methylpyrrolidin-2-yl]ethyl}-1,2,3,4-tetrahydroisoquinoline-7-sulfonamide hemifumarate comprises heating 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate above about ambient temperatures, wherein ambient temperature ranges from about 20 to about 25° C.

In another aspect of the invention, a process for preparing 2-(cyclohexylmethyl)-N-{2-[(2S)-1-methylpyrrolidin-2-yl]ethyl}-1,2,3,4-tetrahydroisoquinoline-7-sulfonamide hemifumarate comprises heating 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate above room temperature, for example above about 40° C., at low relative humidity, for example below about 19% humidity.

Another aspect of the invention is 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate. A particular aspect of the invention is 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate in crystalline form. The crystalline form of 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate described in this specification is referred to as 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate Form I. In one aspect of the invention, the crystalline form of 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate exhibits an X-ray diffraction pattern comprising peaks at about 3.49, 6.93, 8.46, 10.34, 13.25, 13.75, and 15.40 degrees 2-theta.

The present invention also provides a process for preparing 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate comprising contacting 2-(cyclohexylmethyl)-N-{2-[2S)-1-methylpyrrolidin-2-yl]ethyl}-1,2,3,4-tetrahydroisoquinoline-7-sulfonamide hemifumarate with water.

Another aspect of the invention, is the process for preparing 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate comprising exposing 2-(cyclohexylmethyl)-N-{2-[(2S)-1-methylpyrrolidin-2-yl]ethyl}-1,2,3,4-tetrahydroisoquinoline-7-sulfonamide hemifumarate to above about 20% relative humidity at around ambient temperature, wherein ambient temperature ranges from 20 to 25° C.

The present invention provides pharmaceutical compositions comprising 2-(cyclohexyl methyl)-N-{2-[(2S)-1-methylpyrrolidin-2-yl]ethyl}-1,2,3,4-tetrahydroisoquinoline-7-sulfonamide difumarate monohydrate in combination with a pharmaceutically acceptable carrier. In one aspect of the invention, the pharmaceutical composition comprises crystalline 2-(cyclohexylmethyl)-N-{2-[(2S)-1-methylpyrrolidin-2-yl]ethyl}-1,2,3,4-tetrahydroisoquinoline-7-sulfonamide difumarate monohydrate in combination with a pharmaceutically acceptable carrier.

The present invention also provides pharmaceutical compositions comprising 2-(cyclohexyl methyl)-N-{2-[(2S)-1-methylpyrrolidin-2-yl]ethyl}-1,2,3,4-tetrahydroisoquinoline-7-sulfonamide difumarate in combination with a pharmaceutically acceptable carrier. In one aspect of the invention, the pharmaceutical composition comprises crystalline 2-(cyclohexyl methyl)-N-{2-[(2S)-1-methylpyrrolidin-2-yl]ethyl}-1,2,3,4-tetrahydroisoquinoline-7-sulfonamide difumarate in combination with a pharmaceutically acceptable carrier.

The present invention also provides pharmaceutical compositions comprising 2-(cyclohexyl methyl)-N-{2-[(2S)-1-methylpyrrolidin-2-yl]ethyl}-1,2,3,4-tetrahydroisoquinoline-7-sulfonamide monofumarate in combination with a pharmaceutically acceptable carrier. In one aspect of the invention, the pharmaceutical composition comprises crystalline 2-(cyclohexylmethyl)-N-{2-[(2S)-1-methylpyrrolidin-2-yl]ethyl}-1,2,3,4-tetrahydroisoquinoline-7-sulfonamide monofumarate in combination with a pharmaceutically acceptable carrier.

The present invention also provides pharmaceutical compositions comprising 2-(cyclohexyl methyl)-N-{2-[(2S)-1-methylpyrrolidin-2-yl]ethyl}-1,2,3,4-tetrahydroisoquinoline-7-sulfonamide hemifumarate in combination with a pharmaceutically acceptable carrier. In one aspect of the invention, the pharmaceutical composition comprises crystalline 2-(cyclohexyl methyl)-N-{2-[(2S)-1-methylpyrrolidin-2-yl]ethyl}-1,2,3,4-tetrahydroisoquinoline-7-sulfonamide hemifumarate in combination with a pharmaceutically acceptable carrier.

The present invention also provides pharmaceutical compositions comprising 2-(cyclohexyl methyl)-N-{2-[(2S)-1-methylpyrrolidin-2-yl]ethyl}-1,2,3,4-tetrahydroisoquinoline-7-sulfonamide hemifumarate dihydrate in combination with a pharmaceutically acceptable carrier. In one aspect of the invention, the pharmaceutical composition comprises crystalline 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate in combination with a pharmaceutically acceptable carrier.

Another aspect of the invention is a pharmaceutical composition prepared by formulating the difumarate monohydrate salt with one or more pharmaceutically acceptable carriers.

Another aspect of the invention is a pharmaceutical composition prepared by formulating the difumarate salt with one or more pharmaceutically acceptable carriers.

Another aspect of the invention is a pharmaceutical composition prepared by formulating the monofumarate salt with one or more pharmaceutically acceptable carriers.

Another aspect of the invention is a pharmaceutical composition prepared by formulating the hemifumarate salt with one or more pharmaceutically acceptable carriers.

Another aspect of the invention is a pharmaceutical composition prepared by formulating the hemifumarate dihydrate salt with one or more pharmaceutically acceptable carriers.

The present invention also provides a process for preparing a pharmaceutical composition comprising formulating the difumarate monohydrate salt with one or more pharmaceutically acceptable diluents.

The present invention also provides a process for preparing a pharmaceutical composition comprising formulating the difumarate salt with one or more pharmaceutically acceptable diluents.

The present invention also provides a process for preparing a pharmaceutical composition comprising formulating the monofumarate salt with one or more pharmaceutically acceptable diluents.

The present invention also provides a process for preparing a pharmaceutical composition comprising formulating the hemifumarate salt with one or more pharmaceutically acceptable diluents.

The present invention also provides a process for preparing a pharmaceutical composition comprising formulating the hemifumarate dihydrate salt with one or more pharmaceutically acceptable diluents.

The compounds of the invention may be administered in pharmaceutically acceptable dosage forms to humans and other mammals by topical or systemic administration, including oral, inhalational, rectal, nasal, buccal, sublingual, vaginal, colonic, parenteral (including subcutaneous, intramuscular, intravenous, intradermal, intrathecal and epidural), intracisternal and intraperitoneal. It will be appreciated that the particular route may vary with for example the physiological condition of the recipient.

"Pharmaceutically acceptable dosage forms" refers to dosage forms of the compounds of the invention, and includes, for example, tablets, dragées, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

A particular aspect of the invention provides for the compounds of the invention to be administered in the form of a pharmaceutical composition.

Pharmaceutically acceptable carriers include at least one component selected from the group comprising pharmaceutically acceptable carriers, diluents, coatings, adjuvants, excipients, or vehicles, such as preserving agents, fillers, disintegrating agents, wetting agents, emulsifying agents, stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage forms.

Exemplary suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances.

Exemplary antibacterial and antifungal agents for the prevention of the action of microorganisms include parabens, chlorobutanol, phenol, sorbic acid, and the like.

Exemplary isotonic agents include sugars, sodium chloride, and the like.

Exemplary adsorption delaying agents to prolong absorption include aluminum monostearate and gelatin.

Exemplary adsorption promoting agents to enhance absorption include dimethyl sulfoxide and related analogs.

Exemplary diluents, solvents, vehicles, solubilizing agents, stabilizing agents, emulsifiers and emulsion stabilizers, include water, chloroform, sucrose, ethanol, isopropyl alcohol, ethyl carbonate, ethyl acetate, benzyl alcohol, tetrahydrofurfuryl alcohol, benzyl benzoate, polyols, propylene glycol, 1,3-butylene glycol, glycerol, polyethylene glycols, dimethylformamide, Tween® 60, Span® 60, cetostearyl alcohol, myristyl alcohol, glyceryl mono-stearate and sodium lauryl sulfate, fatty acid esters of sorbitan, vegetable oils (such as cottonseed oil, groundnut oil, olive oil, castor oil and sesame oil) and injectable organic esters such as ethyl oleate, and the like, or suitable mixtures of these substances.

Exemplary excipients include lactose, milk sugar, sodium citrate, calcium carbonate and dicalcium phosphate.

Exemplary disintegrating agents include starch, alginic acids and certain complex silicates.

Exemplary lubricants include magnesium stearate, sodium lauryl sulfate, talc, as well as high molecular weight polyethylene glycols.

Pharmaceutical compositions of the present invention suitable for oral administration may be presented as discrete units such as a solid dosage form, such as capsules, cachets or tablets each containing a predetermined amount of the active ingredient, or as a powder or granules; as a liquid dosage form such as a solution or a suspension in an aqueous liquid or a non-aqueous liquid, or as an oil-in-water liquid emulsion or a water-in-oil liquid emulsion. The active ingredient may also be presented as a bolus, electuary or paste.

"Solid dosage form" means the dosage form of a compound of the invention is in solid form, for example capsules, tablets, pills, powders, dragées or granules. In such solid dosage forms, a compound of the invention is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, (j) opacifying agents, (k) buffering agents, and agents which release a compound of the invention in a certain part of the intestinal tract in a delayed manner.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used. A mixture of the powdered compounds moistened with an inert liquid diluent may be molded in a suitable machine to make molded tablets. The tablets may optionally be coated or scored and may be formulated so as to provide slow or controlled release of the active ingredient therein.

Solid compositions may also be employed as fillers in soft and hard-filled gelatin capsules using such excipients as lactose or milk sugar as well as high molecular weight polyethylene glycols, and the like.

If desired, and for more effective distribution, the compound can be microencapsulated in, or attached to, a slow release or targeted delivery systems such as a biocompatible, biodegradable polymer matrices (e.g., poly(d,l-lactide coglycolide)), liposomes, and microspheres and subcutaneously or intramuscularly injected by a technique called subcutaneous or intramuscular depot to provide continuous slow release of the compound(s) for a period of 2 weeks or longer. The compound may be sterilized, for example, by filtration through a bacteria-retaining filter, or by incorporating sterilizing agents in the form of sterile solid compositions which can be dissolved in sterile water, or some other sterile injectable medium immediately before use.

"Liquid dosage form" means the dose of the active compound to be administered to the patient is in liquid form, for example, pharmaceutically acceptable emulsions, solutions, suspensions, syrups and elixirs. In addition to the active compound, the liquid dosage forms may contain inert diluents commonly used in the art, such as solvents, solubilizing agents and emulsifiers.

When aqueous suspensions are used they can contain emulsifying agents or agents which facilitate suspension.

Pharmaceutical compositions suitable for topical administration means formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of the compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The oily phase of the emulsion pharmaceutical composition may be constituted from known ingredients, in a known manner. While the phase may comprise merely an emulsifier (otherwise known as an emulgent), it desirably comprises a mixture of at least one emulsifier with a fat or an oil or with both a fat and an oil. In a particular embodiment, a hydrophilic emulsifier is included together with a lipophilic emulsifier that acts as a stabilizer. Together, the emulsifier(s) with, or without, stabilizer(s) make up the emulsifying wax, and together with the oil and fat make up the emulsifying ointment base which forms the oily dispersed phase of the cream formulations.

If desired, the aqueous phase of the cream base may include, for example, a least 30% w/w of a polyhydric alcohol, i.e. an alcohol having two or more hydroxyl groups such as, propylene glycol, butane 1,3-diol, mannitol, sorbitol, glycerol and polyethylene glycol (including PEG 400) and mixtures thereof. The topical formulations may desirably include a compound that enhances absorption, or penetration of the active ingredient through the skin, or other affected areas.

The choice of suitable oils or fats for a composition is based on achieving the desired properties. Thus a cream should particularly be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Pharmaceutical compositions suitable for rectal or vaginal administrations mean formulations that are in a form suitable to be administered rectally or vaginally to a patient and containing at least one compound of the invention. Suppositories are a particular form for such formulations that can be prepared by mixing a compound of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Pharmaceutical compositions administered by injection may be by transmuscular, intravenous, intraperitoneal, and/or subcutaneous injection. The compositions of the present invention may be formulated in liquid solutions, in particular in physiologically compatible buffers such as Hank's solution or Ringer's solution. In addition, the compositions may be formulated in solid form and redissolved or suspended immediately prior to use. Lyophilized forms are also included. The formulations are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient.

Pharmaceutical compositions of the present invention suitable for nasal or inhalational administration are in a form suitable to be administered nasally or by inhalation to a patient. The composition may contain a carrier, in a powder form, having a particle size for example in the range 1 to 500 microns (including particle sizes in a range between 20 and 500 microns in increments of 5 microns such as 30 microns, 35 microns, etc.). Suitable compositions wherein the carrier is a liquid, for administration as for example a nasal spray or as nasal drops, include aqueous or oily solutions of the active ingredient. Compositions suitable for aerosol administration may be prepared according to conventional methods and may be delivered with other therapeutic agents. Inhalational therapy is readily administered by metered dose inhalers or any suitable dry powder inhaler.

Actual dosage levels of active ingredient(s) in the compositions of the invention may be varied so as to obtain an amount of active ingredient(s) that is (are) effective to obtain a desired therapeutic response for a particular composition and method of administration for a patient. A selected dosage level for any particular patient therefore depends upon a variety of factors including the desired therapeutic effect, the route of administration, the desired duration of treatment, the etiology and severity of the disease, the patient's condition, weight, sex, diet and age, the type and potency of each active ingredient, rates of absorption, metabolism and/or excretion and other factors.

Total daily dose of a compound of this invention administered to a patient in single or divided doses may be in amounts, for example, of from about 0.001 to about 100 mg/kg body weight daily and particularly 0.01 to 10 mg/kg/day. For example, in an adult, the doses are generally from about 0.01 to about 100, particularly about 0.01 to about 10, mg/kg body weight per day by inhalation, from about 0.01 to about 100, particularly 0.1 to 70, more especially 0.5 to 10, mg/kg body weight per day by oral administration, and from about 0.01 to about 50, particularly 0.01 to 10, mg/kg body weight per day by intravenous administration. The percentage of active ingredient in a composition may be varied, though it should constitute a proportion such that a suitable dosage shall be obtained. Dosage unit compositions may contain such amounts of such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much lower maintenance doses adequate. For other patients, it may be necessary to have long-term treatments at the rate of 1 to 4 doses per day, in accordance with the physiological requirements of each particular patient. For other patients, it may be necessary to prescribe not more than one or two doses per day.

The formulations can be prepared in unit dosage form by any of the methods well known in the art of pharmacy. Such methods include the step of bringing into association the pharmaceutically active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

The pharmaceutical compositions of the present invention preferably contain a pharmaceutically effective amount of a compound of the invention. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the mode of administration; the bioavailability characteristics of the preparation administered; the dose regimen selected; the use of concomitant medication; and other relevant circumstances.

The pharmaceutical compositions of the present invention can be administered with other therapeutic and/or prophylactic agents and/or medicaments that are not medically incompatible therewith.

All components of the present compositions must be pharmaceutically acceptable. As used herein, a "pharmaceutically acceptable" component is one that is suitable for use with humans and/or other animals without undue adverse side effects (such as toxicity, irritation and allergic response) commensurate with a reasonable benefit/risk ratio.

The present invention further relates to the use of the pharmaceutical compositions of the invention in medicine.

2-(Cyclohexylmethyl)-N-{2-[(2S)-1-methylpyrrolidin-2-yl]ethyl}-1,2,3,4-tetrahydroisoquinoline-7-sulfonamide is a potent histamine H3 receptor antagonist and, as such, can be used in the treatment of pathologies in which a histamine H3 receptor antagonist provides a therapeutic benefit. In particular, the compounds of the invention can be used in the treatment of obesity, diabetes, central nervous system diseases such as vigilance and sleep disorders, narcolepsy, Alzheimer's disease and other dementias, Parkinson's disease, attention-deficit hyperactivity disorder, memory and learning disorders, epilepsy, schizophrenia, moderate cognitive disorders, depression, and anxiety. The states of depression and anxiety include, for example, anxieties of anticipatory type (before a surgical procedure, before a dental treatment, etc), anxiety caused by alcohol or drug dependency or withdrawal, mania, seasonal affective disorders, migraines and nausea. The compounds of the invention can also be used in the treatment of sexual dysfunction, dizziness and travel sickness. The compounds of the invention can also be used in the treatment of cardiovascular disorders and gastrointestinal disorders.

An aspect of the invention is a method of treating pathologies in which a histamine H3 receptor antagonist provides a therapeutic benefit, which comprises administering to a patient in need of said treatment a pharmaceutically effective amount of a compound selected from the group consisting of 2-(cyclohexylmethyl)-N-{2-[(2S)-1-methylpyrrolidin-2-yl]ethyl}-1,2,3,4-tetrahydroisoquinoline-7-sulfonamide difumarate monohydrate, 2-(cyclohexylmethyl)-N-{2-[(2S)-1-methylpyrrolidin-2-yl]ethyl}-1,2,3,4-tetrahydroisoquinoline-7-sulfonamide difumarate, 2-(cyclohexylmethyl)-N-{2-[(2S)-1-methylpyrrolidin-2-yl]ethyl}-1,2,3,4-tetrahydroisoquinoline-7-sulfonamide monofumarate, 2-(cyclohexylmethyl)-N-{2-[(2S)-1-methylpyrrolidin-2-yl]ethyl}-1,2,3,4-tetrahydroisoquinoline-7-sulfonamide hemifumarate, and 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate or a pharmaceutically effective amount of a pharmaceutical composition of the present invention.

Another aspect of the invention is a method of treating pathologies in which a histamine H3 receptor antagonist provides a therapeutic benefit, which comprises administering to a patient in need of said treatment a pharmaceutically effective amount of 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

In a particular aspect, the present invention provides a method of treating a central nervous system disease, which comprises administering to a patient in need of said treatment a pharmaceutically effective amount of a compound selected from the group consisting of 2-(cyclohexyl methyl)-N-{2-[(2S)-1-methylpyrrolidin-2-yl]ethyl}-1,2,3,4-tetrahydroisoquinoline-7-sulfonamide difumarate hydrate, 2-(cyclohexylmethyl)-N-{2-[(2S)-1-methylpyrrolidin-2-yl]ethyl}-1,2,3,4-tetrahydroisoquinoline-7-sulfonamide difumarate, 2-(cyclohexylmethyl)-N-{2-[(2S)-1-methylpyrrolidin-2-yl]ethyl}-1,2,3,4-tetrahydroisoquinoline-7-sulfonamide monofumarate, 2-(cyclohexylmethyl)-N-{2-[(2S)-1-methylpyrrolidin-2-yl]ethyl}-1,2,3,4-tetrahydroisoquinoline-7-sulfonamide hemifumarate, and 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate, or a pharmaceutically effective amount of a pharmaceutical composition of the present invention.

In another particular aspect, the present invention provides a method of treating a central nervous system disease, which comprises administering to a patient in need of said treatment a pharmaceutically effective amount of 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

A particular aspect of the invention is a method of treating a disease or disorder selected from the group consisting of obesity, diabetes, vigilance disorders, sleep disorders, narcolepsy, Alzheimer's disease, dementia, Parkinson's disease, attention-deficit hyperactivity disorder, memory disorders, learning disorders, epilepsy, schizophrenia, moderate cognitive disorders, depression, anxiety, sexual dysfunction, dizziness, and travel sickness, which comprises administering to a patient in need of said treatment a pharmaceutically effective amount of a compound selected from the group consisting of 2-(cyclohexyl methyl)-N-{2-[(2S)-1-methylpyrrolidin-2-yl]ethyl}-1,2,3,4-tetrahydroisoquinoline-7-sulfonamide difumarate monohydrate, 2-(cyclohexylmethyl)-N-{2-[(2S)-1-methylpyrrolidin-2-yl]ethyl}-1,2,3,4-tetrahydroisoquinoline-7-sulfonamide difumarate, 2-(cyclohexylmethyl)-N-{2-[(2S)-1-methylpyrrolidin-2-yl]ethyl}-1,2,3,4-tetrahydroisoquinoline-7-sulfonamide monofumarate, 2-(cyclohexylmethyl)-N-{2-[(2S)-1-methylpyrrolidin-2-yl]ethyl}-1,2,3,4-tetrahydroisoquinoline-7-sulfonamide hemifumarate, and 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate, or a pharmaceutically effective amount of a pharmaceutical composition of the present invention.

Another particular aspect of the invention is a method of treating Alzheimer's disease which comprises administering to a patient in need of said treatment a pharmaceutically effective amount of a compound selected from the group consisting of 2-(cyclohexylmethyl)-N-{2-[(2S)-1-methylpyrrolidin-2-yl]ethyl}-1,2,3,4-tetrahydroisoquinoline-7-sulfonamide difumarate monohydrate, 2-(cyclohexylmethyl)-N-{2-[(2S)-1-methylpyrrolidin-2-yl]ethyl}-1,2,3,4-tetrahydroisoquinoline-7-sulfonamide difumarate, 2-(cyclohexylmethyl)-N-{2-[(2S)-1-methylpyrrolidin-2-yl]ethyl}-1,2,3,4-tetrahydroisoquinoline-7-sulfonamide monofumarate, 2-(cyclohexyl methyl)-N-{2-[(2S)-1-methylpyrrolidin-2-yl]ethyl}-1,2,3,4-tetrahydroisoquinoline-7-sulfonamide hemifumarate, and 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate, or a pharmaceutically effective amount of a pharmaceutical composition of the present invention.

Another particular aspect of the invention is a method of treating Alzheimer's disease which comprises administering to a patient in need of said treatment a pharmaceutically effective amount of 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

An aspect of the present invention is the use of a compound selected from the group consisting of 2-(cyclohexylmethyl)-N-{2-[(2S)-1-methylpyrrolidin-2-yl]ethyl}-1,2,3,4-tetrahydroisoquinoline-7-sulfonamide difumarate monohydrate, 2-(cyclohexylmethyl)-N-{2-[(2S)-1-methylpyrrolidin-2-yl]ethyl}-1,2,3,4-tetrahydroisoquinoline-7-sulfonamide difumarate, 2-(cyclohexylmethyl)-N-{2-[(2S)-1-methylpyrrolidin-2-yl]ethyl}-1,2,3,4-tetrahydroisoquinoline-7-sulfonamide monofumarate, 2-(cyclohexylmethyl)-N-{2-[(2S)-1-methylpyrrolidin-2-yl]ethyl}-1,2,3,4-tetrahydroisoquinoline-7-sulfonamide hemifumarate, and 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate, in the manufacture of medicinal products for the treatment of pathologies in which a histamine H3 receptor antagonist provides a therapeutic benefit.

Another aspect of the invention is the use 2-(cyclohexylmethyl)-N-{2-[(2S)-1-methylpyrrolidin-2-yl]ethyl}-1,2,3,4-tetrahydroisoquinoline-7-sulfonamide difumarate monohydrate, 2-(cyclohexylmethyl)-N-{2-[(2S)-1-methylpyrrolidin-2-yl]ethyl}-1,2,3,4-tetrahydroisoquinoline-7-sulfonamide difumarate, 2-(cyclohexylmethyl)-N-{2-[(2S)-1-methylpyrrolidin-2-yl]ethyl}-1,2,3,4-tetrahydroisoquinoline-7-sulfonamide monofumarate, 2-(cyclohexylmethyl)-N-{2-[(2S)-1-methylpyrrolidin-2-yl]ethyl}-1,2,3,4-tetrahydroisoquinoline-7-sulfonamide hemifumarate, and 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate for the treatment of pathologies in which a histamine H3 receptor antagonist provides a therapeutic benefit.

Another aspect of the invention is the use 2-(cyclohexylmethyl)-N-{2-[(2S)-1-methylpyrrolidin-2-yl]ethyl}-1,2,3,4-tetrahydroisoquinoline-7-sulfonamide difumarate monohydrate, 2-(cyclohexylmethyl)-N-{2-[(2S)-1-methylpyrrolidin-2-yl]ethyl}-1,2,3,4-tetrahydroisoquinoline-7-sulfonamide difumarate, 2-(cyclohexylmethyl)-N-{2-[(2S)-1-methylpyrrolidin-2-yl]ethyl}-1,2,3,4-tetrahydroisoquinoline-7-sulfonamide monofumarate, 2-(cyclohexylmethyl)-N-{2-[(2S)-1-methylpyrrolidin-2-yl]ethyl}-1,2,3,4-tetrahydroisoquinoline-7-sulfonamide hemifumarate, and 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate for the treatment of a disease or disorder selected from the group consisting of obesity, diabetes, vigilance disorders, sleep disorders, narcolepsy, Alzheimer's disease, dementia, Parkinson's disease, attention-deficit hyperactivity disorder, memory disorders, learning disorders, epilepsy, schizophrenia, moderate cognitive disorders, depression, anxiety, sexual dysfunction, dizziness, and travel sickness.

The preparation and properties of the compounds of the invention are described in the following experimental section. Suitable 2-(cyclohexylmethyl)-N-{2-[(2S)-1-methylpyrrolidin-2-yl]ethyl}-1,2,3,4-tetrahydroisoquinoline-7-sulfonamide starting material for the herein described procedures includes, but is not limited to, 2-(cyclohexylmethyl)-N-{2-[(2S)-1-methylpyrrolidin-2-yl]ethyl}-1,2,3,4-tetrahydroisoquinoline-7-sulfonamide prepared by the procedures described in WO2005/118547.

EXAMPLE 1

Preparation of 2-(cyclohexylmethyl)-N-{2-[(2S)-1-methylpyrrolidin-2-yl]ethyl}-1,2,3,4-tetrahydroisoquinoline-7-sulfonamide difumarate monohydrate 2-(Cyclohexylmethyl)-N-{2-[(2S)-1-methylpyrrolidin-2-yl]ethyl}-1,2,3,4-tetrahydroisoquinoline-7-sulfonamide (318 mg, 0.756 mmol) was dissolved in methanol (3 mL). Fumaric acid solution (29 mg/3 mL, 2.1 equivalents) was added. The mixture was dried at room temperature under vacuum. The recovered solid was dissolved in isopropanol (1 mL). One milliliter of ethyl acetate was added and the solution was placed in refrigerator. The solids were collected by vacuum filtration.

EXAMPLE 2

Preparation of 2-(cyclohexylmethyl)-N-{2-[(2S)-1-methylpyrrolidin-2-yl]ethyl}-1,2,3,4-tetrahydroisoquinoline-7-sulfonamide difumarate monohydrate Prepared with Seeding Step 2-(Cyclohexylmethyl)-N-{2-[(2S)-1-methylpyrrolidin-2-yl]ethyl}-1,2,3,4-tetrahydroisoquinoline-7-sulfonamide (43.7 g, 104 mmol) was dissolved in 95% ethanol (200 mL) with warming on a steam bath. Fumaric acid (23.8 g, 203 mmol, 1.95 equivalents) was added, rinsing the flask with 95% ethanol (50 mL). The mixture was heated with swirling to near boiling on the steam bath until all of the fumaric acid dissolved. The solution was removed from the steam bath and allowed to stir at room temperature. When the temperature of the solution reached 48° C., it was seeded with previously isolated 2-(cyclohexyl methyl)-N-{2-[(2S)-1-methylpyrrolidin-2-yl]ethyl}-1,2,3,4-tetrahydroisoquinoline-7-sulfonamide difumarate monohydrate. The mixture was allowed to cool and by 27.7° C., it had largely set up. After standing over the weekend, the mixture was cooled in an ice bath. The solids were collected and washed with ice-cold 95% ethanol (175 mL). After air-drying overnight, the clumps were partially broken up to give a colorless solid: 58.4 g (84% yield).

The difumarate monohydrate salt was recrystallized from 95% ethanol (350 mL), seeding with previously isolated 2-(cyclohexylmethyl)-N-{2-[(2S)-1-methylpyrrolidin-2-yl]ethyl}-1,2,3,4-tetrahydroisoquinoline-7-sulfonamide difumarate monohydrate and stirring while cooling to room temperature. The mixture became very thick, finally setting up enough that stirring effectively stopped. After standing at room temperature overnight, the mixture was cooled in ice bath and the solids were collected by filtration. The filtrate was washed through the filter cake with ice-cold 95% ethanol (50 mL). The filter cake was then washed with ice-cold ethanol (125 mL) and air-dried overnight to give the desired product as a colorless solid: 49.84 g (72% yield).

EXAMPLE 3

Preparation of 2-(cyclohexylmethyl)-N-{2-[(2S)-1-methylpyrrolidin-2-yl]ethyl}-1,2,3,4-tetrahydroisoquinoline-7-sulfonamide difumarate 2-(Cyclohexylmethyl)-N-{2-[(2S)-1-methylpyrrolidin-2-yl]ethyl}-1,2,3,4-tetrahydroisoquinoline-7-sulfonamide difumarate monohydrate (solid, 50 mg) was heated at a linear rate of 1.8° C./minute to 80° C. at ambient RH and held for 50 minutes to yield the difumarate salt.

EXAMPLE 4

Preparation of 2-(cyclohexylmethyl)-N-{2-[(2S)-1-methylpyrrolidin-2-yl]ethyl}-1,2,3,4-tetrahydroisoquinoline-7-sulfonamide hemifumarate anhydrate 2-(Cyclohexylmethyl)-N-{2-[(2S)-1-methylpyrrolidin-2-yl]ethyl}-1,2,3,4-tetrahydroisoquinoline-7-sulfonamide difumarate monohydrate (17.19 g, 25.7 mmol) was suspended in about 225 mL of water. Potassium carbonate (15.3 g, 111 mmol) was added, and the mixture was extracted into ethyl acetate. The organic extract was washed twice with water. An additional 5 mL of brine was added to the 2nd wash to break up the emulsion. The liquid was concentrated in vacuo. Acetone (about 50 mL) was added and the material was concentrated in vacuo. The residue was dissolved in 60 mL of acetone, and polish filtered into a flask (2×20 mL rinses). A solution of the fumaric acid (2.98 g, 25.7 mmol) in 100 mL of acetone and 20 mL of 95% ethanol was added with stirring. The solution turned permanently cloudy at the end of the addition with the separation of a clear oil. The material was heated briefly on a steam bath to boiling, then about 15 mL of 95% EtOH was added to dissolve the oil. The material was stirred at room temperature overnight. The precipitated solids were filtered and washed with 50 mL of acetone containing 10% ethanol (95%). The cake was air dried for about 6 hours in the hood, and gave 4.17 g of 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

After standing, additional crystals formed in the filtrate. The crystals were collected and washed with acetone containing a small amount of 95% ethanol to give, after air drying, 1.08 g of white needles. The isolated material is 2-(cyclohexylmethyl)-N-{2-[(2S)-1-methylpyrrolidin-2-yl]ethyl}-1,2,3,4-tetrahydroisoquinoline-7-sulfonamide hemifumarate.

EXAMPLE 5

Preparation of 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate 2-(Cyclohexylmethyl)-N-{2-[(2S)-1-methylpyrrolidin-2-yl]ethyl}-1,2,3,4-tetrahydroisoquinoline-7-sulfonamide hemifumarate anhydrate (solid, 10 mg) was allowed to stand at 25° C. and 60% RH for 2 hours. After 2 hours the sample had fully transformed to the hemifumarate dihydrate salt.

EXAMPLE 6

Preparation of 2-(Cyclohexylmethyl)-N-{2-[(2S)-1-methylpyrrolidin-2-yl]ethyl}-1,2,3,4-tetrahydroisoquinoline-7-sulfonamide monofumarate Fumaric acid (1.86 g, 16 mmol) was added to 2-(cyclohexylmethyl)-N-{2-[(2S)-1-methylpyrrolidin-2-yl]ethyl}-1,2,3,4-tetrahydroisoquinoline-7-sulfonamide (6.7 g, 16 mmol). DMF (10 mL) and water (500 µL) were added to the mixture, and the solids were dissolved by warming on a steam bath. Isopropyl acetate (30 mL) was added gradually while heating on a steam bath. The heat was removed, and material oiled out. The mother liquors were decanted. About 100 mL MTBE were added to the residual oil, which was stirred for several hours until the mixture was a uniform slurry. A solid was collected and washed with MTBE. The solid was harvested and dried by vacuum filtration on a Büchner funnel. NMR shows a 1.9:1 ratio of fumaric acid to base. The solid was air-dried over night.

Additional material crystallized from the DMF/isopropyl acetate mother liquors. After refrigeration, more material separated as an oil. The mixture was rewarmed to room temperature to redissolve most of the oil. The solids were collected and washed with a little isopropyl acetate. The wash was combined with the mother liquors. The solid was air dried over night. Yield of 0.95 grams.

More material crystallized from the remaining mother liquor. The solids were collected and air was drawn through cake for ½ hour. Yield 0.7 grams. NMR shows a ratio of 1:1 fumaric acid to base indicating the monofumate salt.

The compounds of the invention are analyzed by the following analytical methods.

Fourier Transform Infrared Spectroscopy (FTIR)

Fourier Transform IR spectra were obtained using a Nicolet Magna-IR Spectrometer 55 attached to a Nicolet Nic-Plan FT-IR microscope. Data acquisition and parameter settings were controlled by Omnic 7.2 software. The samples were placed on a KBr disk and scanned from 4000 $cm^{-1}$ to 400 $cm^{-1}$, 32 times. A spectral resolution of 4 $cm^{-1}$ was used.

The FTIR spectra of the compound prepared generally according Example 2 (see FIG. 2) confirmed salt formation and is consistent with the chemical structure of 2-(cyclohexylmethyl)-N-{2-[(2S)-1-methylpyrrolidin-2-yl]ethyl}-1,2,3,4-tetrahydroisoquinoline-7-sulfonamide difumarate monohydrate. Table 1 gives the characteristic wavenumbers for 2-(cyclohexylmethyl)-N-{2-[(2S)-1-methylpyrrolidin-2-yl]ethyl}-1,2,3,4-tetrahydroisoquinoline-7-sulfonamide difumarate monohydrate. The multiple strong bands present in the region of 2800 to 2000 $cm^{-1}$ arise from overtone and combination stretching vibrations of the protonated amine group, consistent with amine salt formation. The C—O stretching vibrations (1650-1550 $cm^{-1}$) characteristic of the carboxylate ion may be considered consistent with salts formed from fumaric acid.

TABLE 1

Characteristic wavenumbers for 2-(cyclohexylmethyl)-N-{2-[(2S)-1-methylpyrrolidin-2-yl]ethyl}-1,2,3,4-tetrahydroisoquinoline-7-sulfonamide difumarate monohydrate

| Wavenumber ($cm^{-1}$ +/− 1 $cm^{-1}$) |
|---|
| 3436 |
| 3243 |
| 3049 |
| 2930 |
| 2851 |
| 2656 |
| 2587 |
| 2504 |
| 1698 |
| 1647 |
| 1634 |
| 1580 |
| 1449 |
| 1332 |
| 1302 |
| 155 |
| 983 |

Differential Scanning calorimetry—Thermal Gravimetric Analysis and Mass Spectrometry (DSC-TGA-MS)

Thermal analysis of the compounds of the invention is performed using a TA Instruments Model Q-600 Simultaneous Differential Scanning calorimeter/Thermal Gravimetric Analyzer (DSC-TGA) under a dry helium atmosphere (100 mL/min) interfaced to a Pfeiffer Quadstar mass spectrometer (DSC-TGA-MS) using a capillary held at 200° C. The DSC-TGA temperature is calibrated using an indium standard and MS with water vapor. MS detection was by a secondary electron multiplier. The compound powder is transferred to an aluminum pan (TA Instruments part number 900793.901). The thermogram is acquired at a linear heating rate of 10° C. per minute.

Thermal analysis for the difumarate monohydrate salt (FIG. 3) shows a loss of water (about 3.3%) during heating up from ambient room temperature to about 100° C. The anhydrous phase, created upon the loss of water, melts at 113 to 123° C. under these conditions.

Figure 6:
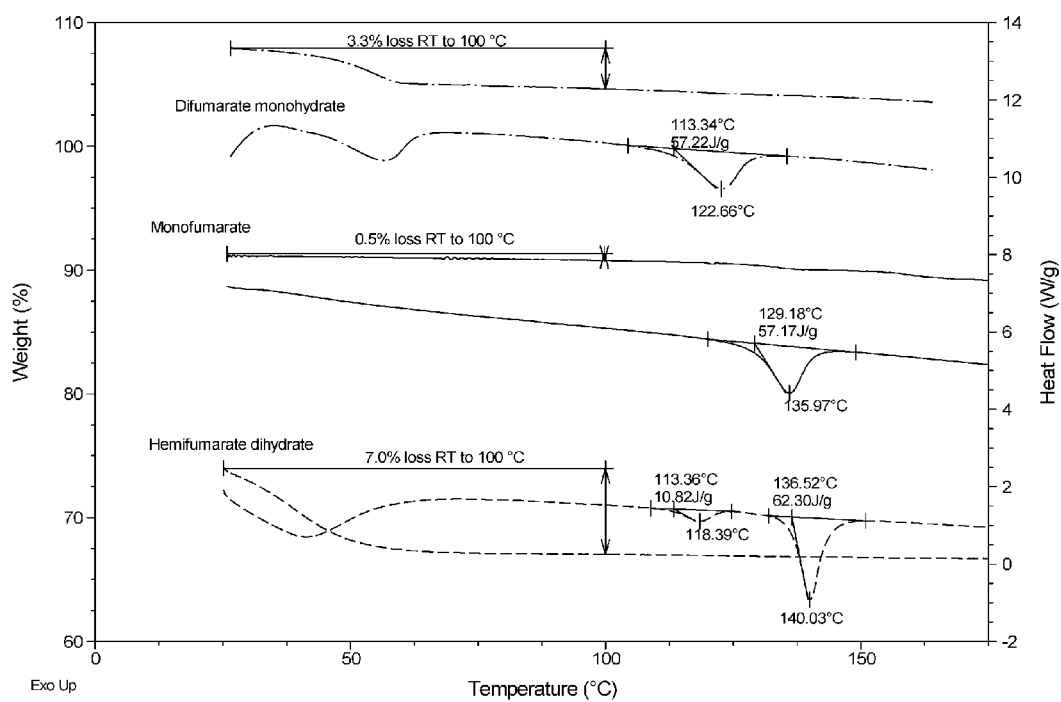
FIG. 6 is an overlay of DSC-TGA thermograms of 2-(cyclohexylmethyl)-N-{2-[(2S)-1-methylpyrrolidin-2-yl]ethyl}-1,2,3,4-tetrahydroisoquinoline-7-sulfonamide difumarate monohydrate, 2-(cyclohexylmethyl)-N-{2-[(2S)-1-methylpyrrolidin-2-yl]ethyl}-1,2,3,4-tetrahydroisoquinoline-7-sulfonamide monofumarate, and 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate of the present invention.

FIG. 6 is an overlay of the thermal (DSC-TGA) profiles of the monofumarate salt with the hemifumarate dihydrate salt and the difumarate monohydrate salt. The DSC of the monofumarate salt shows the melt of the crystalline phase at an onset of 129° C. The melting temperature of the monofumarate salt is unique compared to that of the anhydrous difumarate salt (onset 113° C.) and anhydrous hemifumarate salt (onset 137° C.) salts.

The DSC of the hemifumarate dihydrate salt shows a broad endotherm concomitant with water evolution followed by melt endotherms at onsets of 113° C. (minor) and 137° C. (major). The 137° C. melt is unique to the hemifumarate anhydrate salt while the minor melting endotherm is consistent with the observed melting temperature of the difumarate anhydrate salt.

X-Ray Power Diffractometry (XRPD)

X-ray powder diffractometry is performed on a Siemens-Bruker D5000 diffractometer, using the parafocusing Bragg-Brentano (theta-two-theta)-type geometry. The compound of the invention, as a powder, is deposited on a single-crystal silicon wafer, cut according to the (510) crystallographic orientation. Copper K-alpha radiation (1.54056 angstroms), emitted from a copper anticathode tube (45 kV/40 mA) is used as the x-ray source, with Cu K-beta radiation filtered out using a reflected beam monochromator. A scintillation counter is used for detection. A divergence slit of 0.6 mm, an anti-scatter slit of 0.6 mm, a monochromator slit of 0.1 mm, and detector slit of 0.6 mm are used. The diffraction pattern is obtained using the following conditions: at least 2.0 to 30.0 degree scan in angle 2-theta, 1.0 second count time per step, 0.02 degree step size, under ambient conditions of pressure, temperature, and relative humidity except as noted. Above ambient temperatures were achieved by heating the sample at a linear rate of 0.03 to 0.06° C./second.

The XRPD spectra (FIG. 1) confirmed that the 2-(cyclohexylmethyl)-N-{2-[(2S)-1-methylpyrrolidin-2-yl]ethyl}-1,2,3,4-tetrahydroisoquinoline-7-sulfonamide difumarate monohydrate was crystalline.

Based on the XRPD patterns, the crystalline difumarate anhydrate salt (FIG. 4) has a unique XRPD pattern compared to the crystalline difumarate monohydrate salt.

Figure 5:
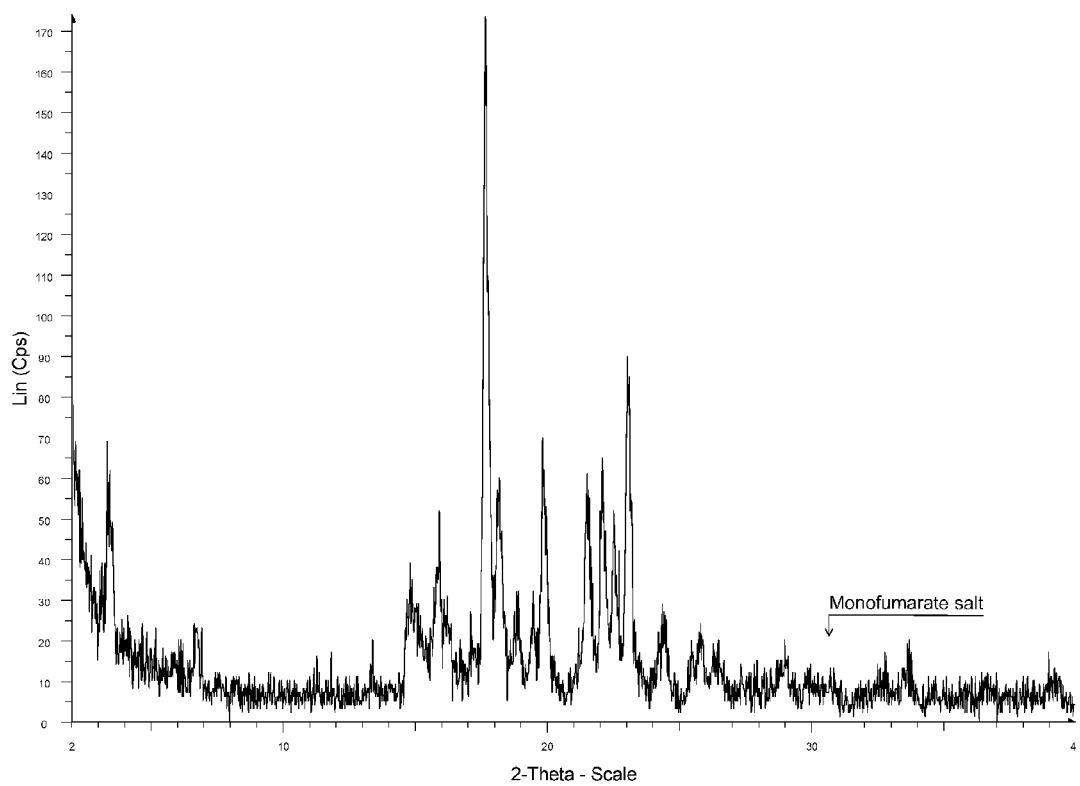
FIG. 5 is an X-ray powder diffractogram of crystalline 2-(cyclohexylmethyl)-N-{2-[(2S)-1-methylpyrrolidin-2-yl]ethyl}-1,2,3,4-tetrahydroisoquinoline-7-sulfonamide monofumarate of the present invention.

FIG. 5 is an XRPD pattern of the crystalline monofumarate salt. The data show that the monofumarate salt crystal structure is unique compared to the crystal structures of the difumarate, difumarate monohydrate, hemifumarate and hemifumarate dihydrate salts.

Figure 7:
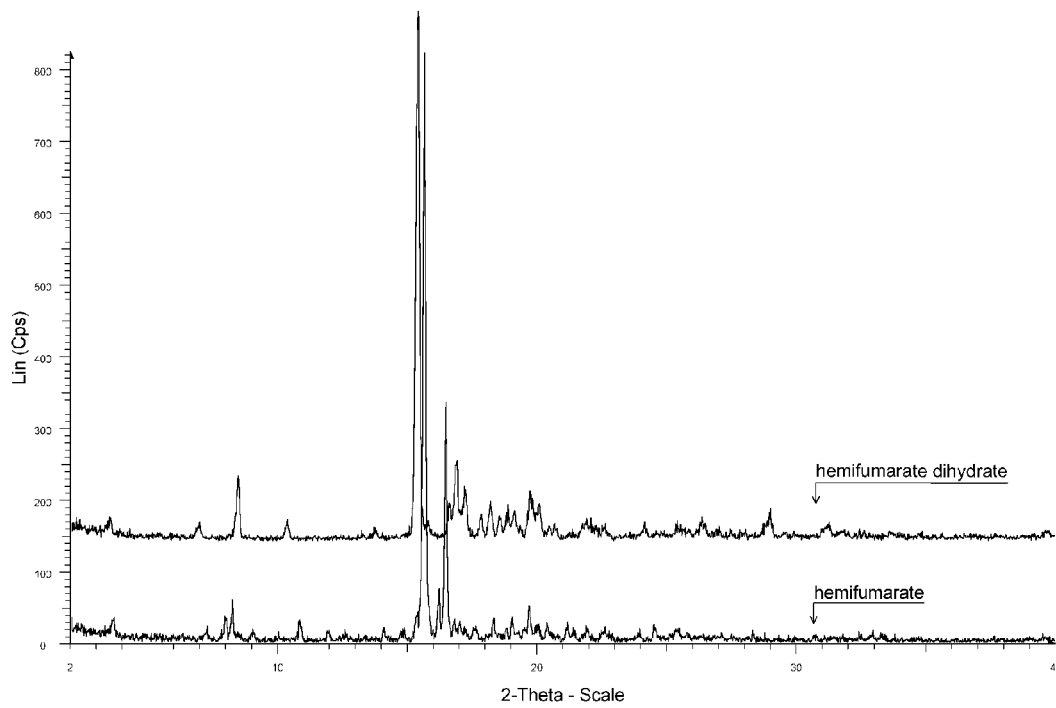
FIG. 7 is an overlay of X-ray powder diffractograms of crystalline 2-(cyclohexylmethyl)-N-{2-[(2S)-1-methylpyrrolidin-2-yl]ethyl}-1,2,3,4-tetrahydroisoquinoline-7-sulfonamide hemifumarate and crystalline 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate of the present invention.

FIG. 7 is an overlay of the XRPD patterns of the crystalline hemifumarate and the crystalline hemifumarate dihydrate salts. The XRPD pattern of the hemifumarate dihydrate salt and corresponding hemifumarate anhydrate salt are largely unique compared to the difumarate monohydrate, difumarate anhydrate and monofumarate salts.

A person skilled in the art will recognize that the peak locations could be slightly affected by differences in sample height. The peak locations described herein are thus subject to a variation of plus or minus (+/−) 0.15 degrees 2-theta. The relative intensities may change depending on the crystal size and morphology.

Table 2 sets forth the characteristic peak locations, d-spacings and relative intensities for the powder x-ray diffraction pattern for the difumarate monohydrate salt.

TABLE 2

Characteristic XRPD Peak locations and Relative Intensities of the Difumarate Monohydrate Salt

| Measured Angle Degrees 2θ +/− 0.15° 2θ | Calculated Spacing d value (Angstroms) | Relative Intensity (%) |
|---|---|---|
| 5.31 | 16.62 | 7.1 |
| 5.84 | 15.12 | 69.6 |
| 7.00 | 12.62 | 27.4 |
| 8.67 | 10.19 | 11.3 |
| 11.71 | 7.55 | 6.5 |
| 13.99 | 6.33 | 8.3 |
| 17.17 | 5.16 | 13.1 |
| 17.59 | 5.04 | 20.8 |
| 18.45 | 4.81 | 100 |
| 19.32 | 4.59 | 13.1 |
| 21.05 | 4.22 | 15.5 |
| 21.69 | 4.09 | 25.0 |

In particular, the peaks at 5.31, 5.84, 7.00, and 8.67 (expressed in degrees 2-theta +/−0.15 degree) are characteristic of the difumarate monohydrate salt.

Table 3 sets forth the characteristic peak locations, d-spacings and relative intensities for the powder x-ray diffraction pattern for the difumarate salt.

TABLE 3

Characteristic XRPD Peak locations and Relative Intensities of the Difumarate Salt

| Measured Angle Degrees 2θ +/− 0.15° 2θ | Calculated Spacing d value (Angstroms) | Relative Intensity (%) |
|---|---|---|
| 5.21 | 16.94 | 17.6 |
| 5.67 | 15.57 | 38.3 |
| 7.06 | 12.51 | 24.3 |
| 11.34 | 7.79 | 36.0 |
| 11.70 | 7.56 | 26.6 |
| 13.24 | 6.68 | 9.0 |
| 14.17 | 6.25 | 7.7 |
| 17.01 | 5.21 | 67.1 |
| 17.46 | 5.08 | 35.6 |
| 17.80 | 4.98 | 26.6 |
| 18.54 | 4.78 | 100 |
| 20.87 | 4.25 | 52.3 |
| 21.36 | 4.16 | 51.4 |
| 22.75 | 3.90 | 59.9 |
| 23.68 | 3.76 | 14.9 |
| 24.15 | 3.68 | 20.3 |
| 25.53 | 3.49 | 24.3 |

In particular, the peaks at 5.21, 5.67, 7.06, and 11.34 (expressed in degrees 2-theta +/−0.15 degrees 2-theta) are characteristic of the difumarate salt.

Table 4 sets forth the characteristic peak locations, d-spacings and relative intensities for the powder x-ray diffraction pattern for the monofumarate salt.

TABLE 4

Characteristic XRPD Peak Locations and Relative Intensities of the Monofumarate Salt

| Measured Angle Degrees 2θ +/− 0.15° 2θ | Calculated Spacing d value (Angstroms) | Relative Intensity (%) |
|---|---|---|
| 3.37 | 26.24 | 33.9 |
| 6.70 | 13.19 | 13.2 |
| 13.36 | 6.62 | 11.1 |
| 14.83 | 5.97 | 22.4 |
| 15.88 | 5.58 | 29.9 |
| 17.65 | 5.02 | 100 |
| 18.16 | 4.88 | 34.5 |
| 18.84 | 4.71 | 18.4 |
| 19.45 | 4.56 | 18.4 |
| 19.87 | 4.46 | 35.6 |
| 21.52 | 4.13 | 35.1 |
| 22.09 | 4.02 | 37.4 |
| 22.52 | 3.95 | 29.9 |
| 23.06 | 3.85 | 51.7 |
| 24.42 | 3.64 | 15.5 |
| 25.81 | 3.45 | 13.8 |

In particular, the peaks at 3.37, 6.70, 13.36, 14.83, 15.88, and 17.65 (expressed in degrees 2-theta +/−0.15 degrees 2-theta) are characteristic of the monofumarate salt.

Table 5 sets forth the characteristic peak locations, d-spacings and relative intensities for the powder x-ray diffraction pattern for the hemifumarate salt.

TABLE 5

Characteristic XRPD Peak Locations and Relative Intensities of the Hemifumarate Salt

| Measured Angle Degrees 2θ +/− 0.15° 2θ | Calculated Spacing d value (Angstroms) | Relative Intensity (%) |
|---|---|---|
| 3.61 | 24.48 | 3.9 |
| 7.22 | 12.24 | 2.3 |
| 7.96 | 11.10 | 4.5 |
| 8.21 | 10.76 | 7.3 |
| 9.01 | 9.80 | 2.3 |
| 10.82 | 8.17 | 3.9 |
| 11.93 | 7.41 | 1.8 |
| 12.60 | 7.02 | 2.2 |
| 14.10 | 6.28 | 2.5 |
| 14.82 | 5.97 | 2.3 |
| 15.66 | 5.66 | 100 |
| 16.19 | 5.47 | 9.1 |
| 16.47 | 5.38 | 40.7 |

In particular, the peaks at 3.61, 7.22, 7.96, 8.21, 9.01, 10.82, and 15.66 (expressed in degrees 2-theta +/−0.15 degrees 2-theta) are characteristic of the hemifumarate salt.

Table 6 sets forth the characteristic peak locations, d-spacings and relative intensities for the powder x-ray diffraction pattern for the hemifumarate dihydrate salt.

TABLE 6

Characteristic XRPD Peak Locations and Relative Intensities of the Hemifumarate Dihydrate Salt

| Measured Angle Degrees 2θ +/− 0.15° 2θ | Calculated Spacing d value (Angstroms) | Relative Intensity (%) |
|---|---|---|
| 3.49 | 25.29 | 4.5 |
| 6.93 | 12.75 | 2.7 |
| 8.46 | 10.45 | 12.1 |
| 10.34 | 8.55 | 4.0 |
| 13.25 | 6.68 | 1.9 |
| 13.75 | 6.43 | 2.4 |
| 15.40 | 5.75 | 100.0 |
| 15.77 | 5.61 | 4.6 |
| 16.61 | 5.33 | 7.2 |
| 16.86 | 5.25 | 14.3 |
| 17.21 | 5.15 | 10.3 |
| 17.84 | 4.97 | 5.0 |
| 18.20 | 4.87 | 7.4 |
| 18.55 | 4.78 | 4.7 |
| 18.86 | 4.70 | 6.7 |
| 19.11 | 4.64 | 5.7 |
| 19.75 | 4.49 | 9.4 |
| 20.07 | 4.42 | 7.0 |

In particular, the peaks at 3.49, 6.93, 8.46, 10.34, 13.25, 13.75, and 15.40 (expressed in degrees 2-theta +/−0.15 degrees 2-theta) are characteristic of the hemifumarate dihydrate salt.

Dynamic Vapor Sorption

The water sorption profile of a compound of the invention is determined using a SMS Instruments Dynamic Vapor Sorption Analyzer (DVS) Model DVS-Advantage. Relative humidity (RH) and weight are calibrated using standards. The powder of the relevant compound of the invention is loaded and dried at 0% RH for 3 hours prior to starting the experiment. The RH is stepped from 0.1 to 94.4% in 11 steps. The specimen weight is considered constant at each step when percent mass change is less than 0.01% over a 5-minute interval with a minimum absolute equilibration time of 15 minutes and maximum equilibration time of 180 minutes.

Figure 8:
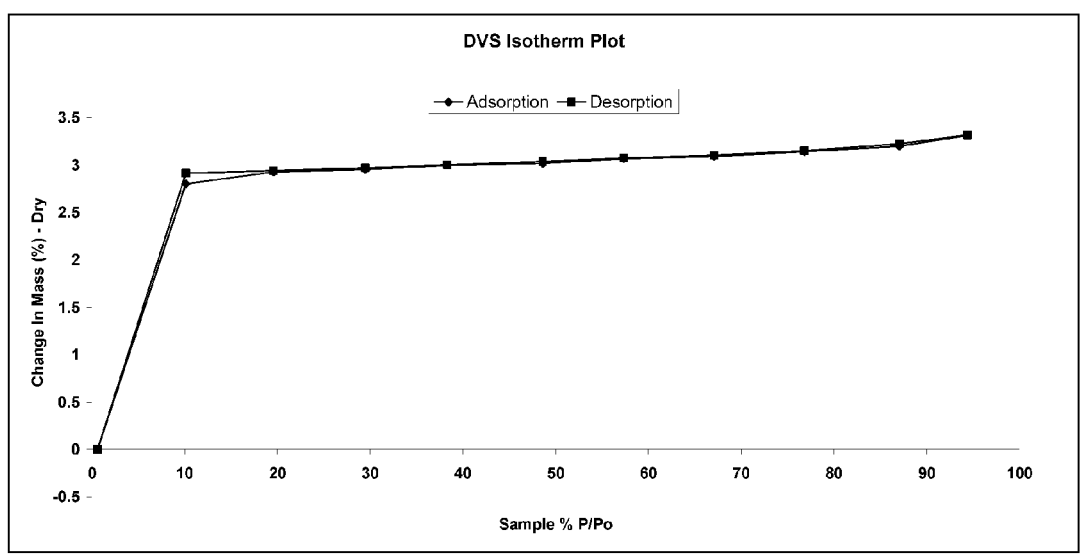
FIG. 8 is the dynamic vapor sorption (DVS) water sorption profile of 2-(cyclohexylmethyl)-N-{2-[(2S)-1-methylpyrrolidin-2-yl]ethyl}-1,2,3,4-tetrahydroisoquinoline-7-sulfonamide difumarate and corresponding 2-(cyclohexylmethyl)-N-{2-[(2S)-1-methylpyrrolidin-2-yl]ethyl}-1,2,3,4-tetrahydroisoquinoline-7-sulfonamide difumarate monohydrate of the present invention.

FIG. 8 is the DVS profile of the difumarate monohydrate salt and corresponding difumarate salt and numerical data is shown in Table 7. The profile shows that the difumarate monohydrate salt is stable from 10% to 94% RH at 25° C.

TABLE 7

Numerical DVS data for the difumarate monohydrate salt and the corresponding difumarte salt

| Sample (% RH) | Change in Mass (%) - dry | |
|---|---|---|
| | Sorption | Desorption |
| 0.6 | 0.0 | 0.0 |
| 10.2 | 2.8 | 2.9 |
| 19.6 | 2.9 | 2.9 |
| 29.4 | 3.0 | 3.0 |
| 38.5 | 3.0 | 3.0 |
| 48.5 | 3.0 | 3.0 |
| 57.5 | 3.1 | 3.1 |
| 67.1 | 3.1 | 3.1 |
| 77.0 | 3.1 | 3.2 |
| 87.0 | 3.2 | 3.2 |
| 94.2 | 3.3 | 3.3 |

Figure 9:
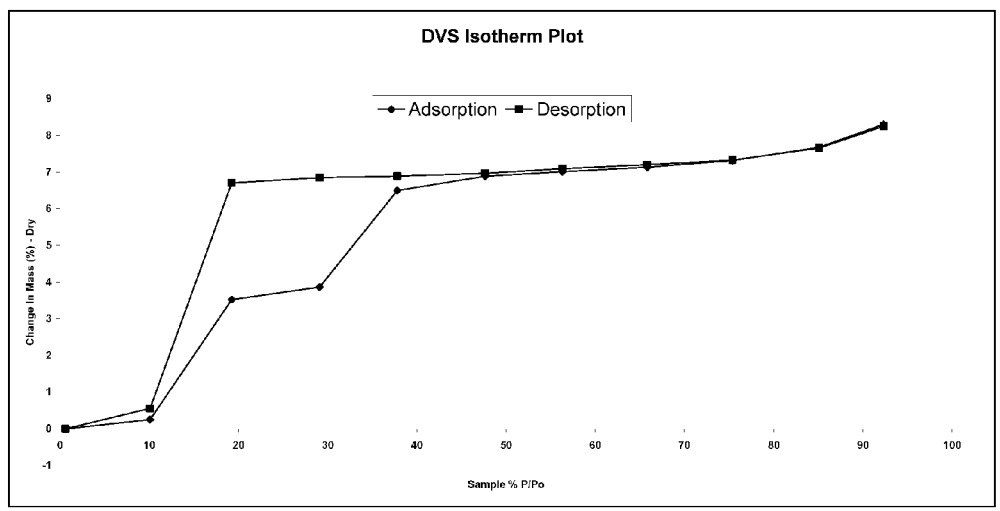
FIG. 9 is the DVS hydgroscopicity profile of 2-(cyclohexylmethyl)-N-{2-[(2S)-1-methylpyrrolidin-2-yl]ethyl}-1,2,3,4-tetrahydroisoquinoline-7-sulfonamide hemifumarate dihydrate and corresponding 2-(cyclohexylmethyl)-N-{2-[(2S)-1-methylpyrrolidin-2-yl]ethyl}-1,2,3,4-tetrahydroisoquinoline-7-sulfonamide hemifumarate of the present invention.

FIG. 9 is the DVS profile of the hemifumarate dihydrate and corresponding hemifumarate salts and numerical data is shown in Table 8. The profile shows that the hemifumarate monohydrate salt is stable from 19% to 92% RH at 25° C.

TABLE 8

Numerical DVS data for the hemifumarate dihydrate and the corresponding hemifumarte salt

| Sample (% RH) | Change in Mass (%) - dry | |
|---|---|---|
| | Sorption | Desorption |
| 0.6 | 0.00 | 0.00 |
| 10.1 | 0.25 | 0.56 |
| 19.4 | 3.53 | 6.71 |
| 29.0 | 3.87 | 6.85 |
| 37.8 | 6.50 | 6.89 |
| 47.7 | 6.89 | 6.97 |
| 56.4 | 7.01 | 7.10 |
| 65.7 | 7.13 | 7.21 |
| 75.3 | 7.32 | 7.33 |
| 84.8 | 7.68 | 7.66 |
| 92.0 | 8.31 | 8.25 |

Stability Testing
1. Storage at 60° C. and Ambient RH for Two Weeks.

Approximately 400 mg of the difumarate monohydrate salt was weighed into a scintillation vial and placed into an oven set to 60° C. The sample was tested for appearance, then diluted with ethanol to approximately 1 mg/mL and analyzed for related substances and optical enantiomer by HPLC.

After storage at 60° C. for 14 days, the difumarate monohydrate salt showed no observable change in physical form by XRPD and DSC-TGA. The difumarate monohydrate appears to be physically stable under these storage conditions. With respect to chemical stability, the difumarate monohydrate salt appears to be stable in the solid state with a minimal increase in impurity levels and no observable change in appearance.

2. Storage at 60° C./80% RH and Ambient RH for Two Weeks.

A glass desiccation chamber was pre-equilibrated overnight with a saturated KBr solution to 79.3% RH within an 80° C. oven. Approximately 400 mg of the difumarate monohydrate was weighed into a scintillation vial and placed into the chamber, which was then sealed to maintain the environment. Samples were tested for appearance, then diluted with ethanol to approximately 1 mg/mL and analyzed for related substances and optical enantiomer by HPLC.

After storage at 60° C./80% RH for 14 days, the difumarate monohydrate salt showed no observable change in physical form by XRPD and DSC-TGA. The difumarate monohydrate salt appears to be physically stable under these storage conditions. With respect to chemical stability, the difumarate monohydrate salt appears to be stable in the solid state with a minimal increase in impurity levels and no observable change in appearance.

3. Storage at 80° C./80% RH for 4 Days

A glass desiccation chamber was pre-equilibrated overnight with a saturated KBr solution to 79.3% RH within an 80° C. oven. Approximately 100 mg of the difumarate monohydrate salt was weighed into respective scintillation vials and these vials were placed into the chamber, which was then sealed to maintain the environment. The sample was tested on day 4 for appearance, then diluted with ethanol to approximately 1 mg/mL and analyzed by HPLC versus a control (time 0) sample.

After storage at 80° C./80% RH for 4 days, the difumarate monohydrate salt was stable in the solid state with no observable chemical change.

What is claimed is:

1. A compound 2-(cyclohexylmethyl)-N-{2-[(2S)-1-methylpyrrolidin-2-yl]ethyl}-1,2,3,4-tetrahydroisoquinoline-7-sulfonamide difumarate monohydrate in the crystalline Form I.

2. A pharmaceutical composition comprising a compound according to claim 1 and a pharmaceutically acceptable carrier.

3. A pharmaceutical composition prepared by formulating a compound according to claim 1 with one or more pharmaceutically acceptable carriers.

4. A process for preparing a pharmaceutical composition comprising formulating a compound according to claim 1 with one or more pharmaceutically acceptable diluents.

5. A process for the manufacture of the 2-(cyclohexylmethyl)-N-{2-[(2S)-1-methylpyrrolidin-2-yl]ethyl}-1,2,3,4-tetrahydroisoquinoline-7-sulfonamide difumarate monohydrate according to claim 1 comprising the steps of contacting, under elevated temperature or at ambient temperature, 2-(cyclohexylmethyl)-N-{2-[(2S)-1-methylpyrrolidin-2-yl]ethyl}-1,2,3,4-tetrahydroisoquinoline-7-sulfonamide dissolved in a suitable solvent or in a mixture of solvents, with fumaric acid, optionally dissolved in a solvent or in a mixture of solvents; and isolating the precipitated solid.

6. The pharmaceutical composition according to claim 3, which is in a solid dosage form.

* * * * *